(12) United States Patent
Haupt et al.

(10) Patent No.: US 8,772,313 B2
(45) Date of Patent: Jul. 8, 2014

(54) BENZENESULFONYL OR SULFONAMIDE COMPOUNDS SUITABLE FOR TREATING DISORDERS THAT RESPOND TO THE MODULATION OF THE SEROTONIN 5-HT$_6$ RECEPTOR

(75) Inventors: Andreas Haupt, Ludwigshafen (DE); Frauke Pohlki, Ludwigshafen (DE); Liliane Unger, Ludwigshafen (DE); Ana Lucia Relo, Ludwigshafen (DE); Karsten Wicke, Ludwigshafen (DE); Min Zhang, Abbott Park, IL (US)

(73) Assignees: Abbott Laboratories, Abbott Park, IL (US); AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/286,387

(22) Filed: Nov. 1, 2011

(65) Prior Publication Data

US 2012/0129883 A1    May 24, 2012

Related U.S. Application Data

(60) Provisional application No. 61/408,733, filed on Nov. 1, 2010.

(51) Int. Cl.

| | | |
|---|---|---|
| A61K 31/435 | (2006.01) | |
| A61K 31/451 | (2006.01) | |
| A61K 31/40 | (2006.01) | |
| A61K 31/403 | (2006.01) | |
| A61P 3/04 | (2006.01) | |
| A61P 25/30 | (2006.01) | |
| A61P 25/28 | (2006.01) | |
| A61P 25/18 | (2006.01) | |
| A61P 25/00 | (2006.01) | |
| C07D 211/28 | (2006.01) | |
| C07D 209/52 | (2006.01) | |
| C07D 221/04 | (2006.01) | |

(52) U.S. Cl.
USPC ........... 514/299; 514/331; 514/429; 514/412; 546/232; 546/112; 548/577; 548/515

(58) Field of Classification Search
USPC .......... 514/299, 331, 429, 412; 546/232, 112; 548/577, 515
See application file for complete search history.

(56) References Cited

U.S. PATENT DOCUMENTS

2003/0069254 A1    4/2003    Berger et al.

FOREIGN PATENT DOCUMENTS

| WO | 02/092585 | 11/2002 |
|---|---|---|
| WO | 2006/010629 | 2/2006 |
| WO | 2007/118899 | 10/2007 |
| WO | 2012/059431 | 5/2012 |

OTHER PUBLICATIONS

Bromidge, S.M. et al., "Phenyl benzenesulfonamides are novel and selective 5-HT6 antagonists: identification of N-(2,5-dibromo-3-fluorophenyl)-4-methoxy-3-piperazi n-1-ylbenzenesulfonamide (Sb-357134)," Bioorg. Med. Chem. Lett (2001) 11(1):55-58.
International Search Report and Written Opinion for Application No. PCT/EP2011/069007 dated Dec. 29, 2011 (10 pages).

*Primary Examiner* — San-Ming Hui
*Assistant Examiner* — Kathrien Cruz
(74) *Attorney, Agent, or Firm* — Lisa V. Mueller; Michael Best & Friedrich LLP

(57) ABSTRACT

The present invention relates to benzenesulfonyl or sulfonamide compounds of formulae IA and IB

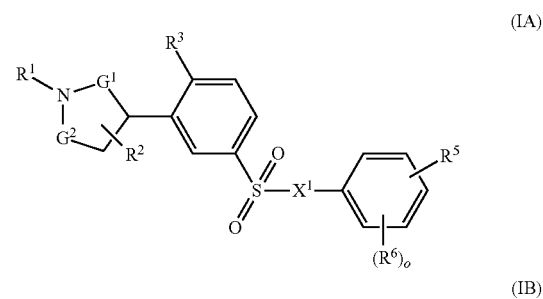

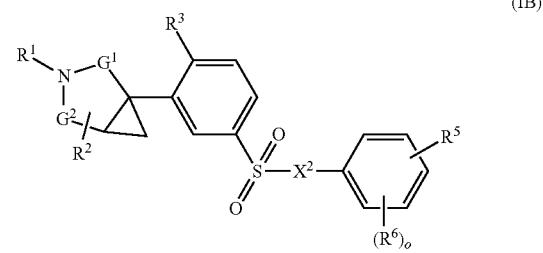

wherein the variables have the meanings given in the claims and the description, pharmaceutical compositions containing them, and their use in therapy. The compounds possess valuable therapeutic properties and are particularly suitable for treating diseases that respond to modulation of the serotonin 5-HT$_6$ receptor.

21 Claims, No Drawings

BENZENESULFONYL OR SULFONAMIDE COMPOUNDS SUITABLE FOR TREATING DISORDERS THAT RESPOND TO THE MODULATION OF THE SEROTONIN 5-HT$_6$ RECEPTOR

CROSS-REFERENCE TO RELATED APPLICATIONS

This claims priority to U.S. Provisional Patent Application No. 61/408,733, filed on Nov. 1, 2010, the contents of which are herein incorporated by reference.

BACKGROUND OF THE INVENTION

The present invention relates to benzenesulfonyl or sulfonamide compounds, pharmaceutical compositions containing them, and their use in therapy. The compounds possess valuable therapeutic properties and are particularly suitable for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases and obesity (see e.g. A. Meneses, Drug News Perspect 14(7) (2001) pp. 396-400 and literature cited therein; J. Pharmacol. Sci. Vol. 101 (Suppl. 1), 2006, p. 124. Modulators of the 5HT$_6$-receptor such as PRX-07034 (Epix Pharmaceuticals) have been found in preclinical and clinical studies to be particular useful in the treatment of cognitive dysfunctions, in particular associated with Alzheimer's disease or schizophrenia or in the treatment of obesity (see e.g. http://www.epixpharma.com/products/prx-07034.asp).

WO 98/027081, WO 99/02502, WO 00/12623, WO 00/12073, US 2003/0069233, WO 02/08179, WO 02/92585, WO 2006/010629, WO 2007/118899 and WO 2007/118900 describe certain benzenesulfonanilide compounds having 5HT$_6$ receptor antagonist activity and suggest the use of these compounds for the treatment of medical disorders which are susceptible to the treatment with 5HT$_6$ receptor antagonists such as certain CNS disorders, drug abuse, ADHD, obesity and type II diabetes.

U.S. Pat. No. 6,825,202 and WO 03/014097 describe benzenesulfonyl compounds having 5HT$_6$ receptor activity.

However, there is still an ongoing need for providing compounds having high affinity for the 5-HT$_6$ receptor and which advantageously also show high selectivity to this receptor.

Besides the binding affinity for the 5-HT$_6$ receptor, further properties may be advantageous for the treatment and/or prophylaxis of 5-HT$_6$-dependent disorders, such as, for example:

1.) a selectivity for the 5-HT$_6$ receptor compared with the 5-HT$_{1A}$ receptor, i.e. the quotient of the binding affinity for the 5-HT$_{1A}$ receptor (Ki(5-HT$_{1A}$) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{1A}$)/Ki(5-HT$_6$) means a greater 5-HT$_6$ selectivity;

2.) a selectivity for the 5-HT$_6$ receptor compared with the 5-HT$_{2A}$ receptor, i.e. the quotient of the binding affinity for the 5-HT$_{2A}$ receptor (Ki(5-HT$_{2A}$) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{2A}$)/Ki(5-HT$_6$) means a greater 5-HT$_6$ selectivity.

3.) a selectivity for the 5-HT$_6$ receptor compared with the 5-HT$_{2B}$ receptor, i.e. the quotient of the binding affinity for the 5-HT$_{2B}$ receptor (Ki(5-HT$_{2B}$) (determined in the unit "nanomolar (nM)") and the binding affinity for the 5-HT$_6$ receptor (Ki(5-HT$_6$)) (determined in the unit "nanomolar (nM)"). A larger quotient Ki(5-HT$_{2B}$)/Ki(5-HT$_6$) means a greater 5-HT$_6$ selectivity.

4.) a low affinity to adrenergic receptors, such as α$_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the anti-hypertensive effect of prazosin, terazosin, doxazosin and labetalol or dizziness associated to the blockade of the α$_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

5.) the metabolic stability, for example determined from the half-lives, measured in vitro, in liver microsomes from various species (e.g. rat or human);

6.) no or only low inhibition of cytochrome P450 (CYP) enzymes: cytochrome P450 (CYP) is the name for a super-family of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

7.) a suitable solubility in water (in mg/ml);

8.) suitable pharmacokinetics (time course of the concentration of the compound of the invention in plasma or in tissue, for example brain). The pharmacokinetics can be described by the following parameters: half-life (in h), volume of distribution (in $l \cdot kg^{-1}$), plasma clearance (in $l \cdot h^{-1} \cdot kg^{-1}$), AUC (area under the curve, area under the concentration-time curve, in $ng \cdot h \cdot l^{-1}$), oral bioavailability (the dose-normalized ratio of AUC after oral administration and AUC after intravenous administration), the so-called brain-plasma ratio (the ratio of AUC in brain tissue and AUC in plasma);

9.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radio-labelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It is one object of the present invention to provide compounds which have a high affinity for the $5\text{-HT}_6$ receptor. It is a further object of the present invention to provide compounds which selectively bind to the $5\text{-HT}_6$ receptor. In addition, the substance of the invention should have one or more of the aforementioned advantages 1.) to 9.).

In particular, it is the object of the present invention to provide compounds which have a high affinity and selectivity for the $5\text{-HT}_6$ receptor and which also show no or only low blockade of the hERG channel. The compounds should also have good pharmacological profile, e.g. a good bioavailability and/or a good metabolic stability.

SUMMARY OF THE INVENTION

The invention is based on the object of providing compounds which act as $5HT_6$ receptor ligands. This object is achieved by compounds of formulae IA and IB

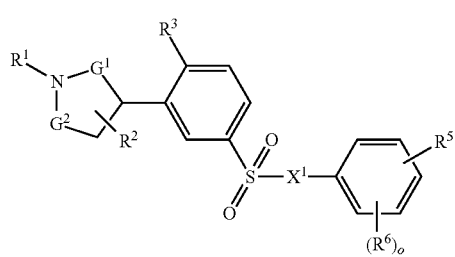

(IA)

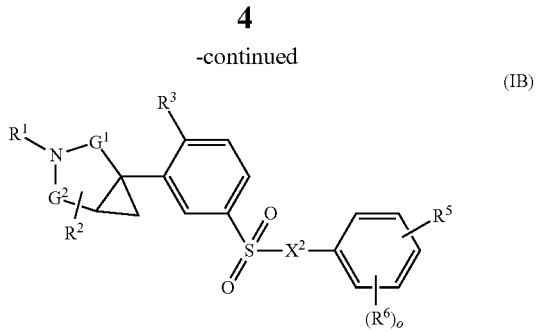

(IB)

the stereoisomers, N-oxides, prodrugs, tautomers and/or physiologically tolerated acid addition salts thereof; and the compounds of the formula I, wherein at least one of the atoms has been replaced by its stable, non-radioactive isotope, wherein $X^1$ is a bond or $NR^4$;

$X^2$ is a bond or $NR^4$;

$R^1$ is selected from hydrogen, $C_1$-$C_4$-alkyl and fluorinated $C_1$-$C_4$-alkyl;

$R^2$ is selected from hydrogen and $C_1$-$C_4$-alkyl;

$R^3$ is selected from hydrogen, halogen, $C_1$-$C_4$-alkyl, fluorinated $C_1$-$C_4$-alkyl, $C_1$-$C_4$-alkoxy and fluorinated $C_1$-$C_4$-alkoxy;

$R^4$ is selected from hydrogen, $C_1$-$C_4$-alkyl and fluorinated $C_1$-$C_4$-alkyl;

$R^5$ is selected from halogen, hydroxyl, $C_1$-$C_6$-alkyl, fluorinated $C_1$-$C_6$-alkyl, $C_1$-$C_6$-hydroxyalkyl, $C_2$-$C_6$-alkenyl, fluorinated $C_2$-$C_6$-alkenyl, $C_3$-$C_6$-cycloalkyl, fluorinated $C_3$-$C_6$-cycloalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, fluorinated $C_1$-$C_6$-alkoxy-$C_1$-$C_6$-alkoxy, a group -A—[O—B—]$_p$—O—$R^7$, $C_1$-$C_6$-alkylthio, fluorinated $C_1$-$C_6$-alkylthio, $C_1$-$C_6$-alkylsulfinyl, fluorinated $C_1$-$C_6$-alkylsulfinyl, $C_1$-$C_6$-alkylsulfonyl, fluorinated $C_1$-$C_6$-alkylsulfonyl, phenylsulfonyl, pyridylsulfonyl, benzyloxy, phenoxy, phenyl, where the phenyl and the pyridyl radical in the 5 last-mentioned radicals may be unsubstituted or may carry 1, 2 or 3 substituents selected from $C_1$-$C_4$-alkyl, fluorinated $C_1$-$C_4$-alkyl and halogen; CN, nitro, $C_1$-$C_6$-alkylcarbonyl, fluorinated $C_1$-$C_6$-alkylcarbonyl, $C_1$-$C_6$-alkylcarbonylamino, fluorinated $C_1$-$C_6$-alkylcarbonylamino, carboxy, NH—C(O)—$NR^8R^9$, $NR^8R^9$, $NR^8R^9$—$C_1$-$C_6$-alkylene, O—$NR^8R^9$, $R^{10}$—CO—$NR^8$—$C_1$-$C_6$-alkylene, $CH_2$-pyridyl, where the pyridyl radical may be unsubstituted or may carry 1 to 3 substituents selected from $C_1$-$C_4$-alkyl, fluorinated $C_1$-$C_4$-alkyl and halogen; and a saturated or unsaturated aromatic or non-aromatic 3-, 4-, 5-, 6- or 7-membered heterocyclic ring comprising as ring members 1, 2, 3 or 4 heteroatoms selected from N, O and S and/or 1, 2 or 3 heteroatom-containing groups selected from $NR^{11}$, SO, $SO_2$ and CO, and where the heterocyclic ring may carry 1, 2 or 3 substituents selected from hydroxy, halogen, $C_1$-$C_6$-alkyl, fluorinated $C_1$-$C_6$-alkyl, $C_1$-$C_6$-alkoxy, fluorinated $C_1$-$C_6$-alkoxy, $C_1$-$C_6$-alkylthio, fluorinated $C_1$-$C_6$-alkylthio, $NR^8R^9$—$C_1$-$C_6$-alkylene, carboxyl and $C_1$-$C_4$-alkoxycarbonyl;

where

A and B are independently of each other $C_1$-$C_4$-alkylene or fluorinated $C_1$-$C_4$-alkylene;

$R^7$ is $C_1$-$C_4$-alkyl or fluorinated $C_1$-$C_4$-alkyl;

$R^8$ and $R^9$ are, independently of each other, H, $C_1$-$C_4$-alkyl, fluorinated $C_1$-$C_4$-alkyl or $C_1$-$C_4$-alkoxy or may form, together with N, a 4-, 5- or 6-membered saturated, partially unsaturated or completely or unsaturated ring;

$R^{10}$ is $C_1$-$C_4$-alkyl or phenyl, where the phenyl radical may be unsubstituted or may carry 1 to 3 substituents selected from $C_1$-$C_4$-alkyl, fluorinated $C_1$-$C_4$-alkyl and halogen;

$R^{11}$ is H, $C_1$-$C_4$-alkyl, fluorinated $C_1$-$C_4$-alkyl, $C_1$-$C_4$-alkylcarbonyl or fluorinated $C_1$-$C_4$-alkylcarbonyl; and p is 0, 1, 2, 3, 4, 5 or 6;

$R^6$ is selected from halogen, $C_1$-$C_2$-alkyl, fluorinated $C_1$-$C_2$-alkyl, $C_1$-$C_2$-alkoxy and fluorinated $C_1$-$C_2$-alkoxy;

$G^1$ is $CH_2$ or $CH_2CH_2$;

$G^2$ is $CH_2$ or $CH_2CH_2$; and o is 0, 1 or 2;

except for compounds IA, wherein $X^1$ is a bond, $R^1$ is hydrogen, $R^2$ is hydrogen or is methyl bound to the carbon atom which is bound to the phenylene group, $R^3$ is methoxy, $R^5$ is 4-Cl, relative to the 1-position of the sulfonyl group $SO_2$, $G^1$ is $CH_2CH_2$, $G^2$ is $CH_2$ and o is 0 (in other words: except for 4-[5-(4-chlorobenzenesulfonyl)-2-methoxy-phenyl]-piperidine and 4-[5-(4-chlorobenzenesulfonyl)-2-methoxy-phenyl]-4-methyl-piperidine);

In particular the present invention relates to compounds IA and IB as defined above, except for compounds IA, wherein $X^1$ is a bond, $R^3$ is methoxy, $R^5$ is 4-Cl, relative to the 1-position of the sulfonyl group $SO_2$, $G^1$ is $CH_2CH_2$, $G^2$ is $CH_2$ and o is 0; or specifically except for compounds IA, wherein $X^1$ is a bond, $R^3$ is $C_1$-$C_4$-alkoxy, $R^5$ is 4-Cl, relative to the 1-position of the sulfonyl group $SO_2$, $G^1$ is $CH_2CH_2$, $G^2$ is $CH_2$ and o is 0; or more specifically except for compounds IA, wherein $X^1$ is a bond, $R^3$ is $C_1$-$C_4$-alkoxy, $R^5$ halogen, fluorinated $C_1$-$C_6$-alkyl, $C_1$-$C_6$-alkoxy, $C_1$-$C_6$-alkylsulfonyl, CN or nitro, $G^1$ is $CH_2CH_2$ and $G^2$ is $CH_2$.

The invention also relates to compounds of formulae IA or IB or the stereoisomers, N-oxides, prodrugs, tautomers or physiologically tolerated acid addition salts thereof or to compounds of formula IA or IB, wherein at least one of the atoms has been replaced by its stable, non-radioactive isotope, for use as a medicament, and to compounds of formulae IA or IB or the stereoisomers, N-oxides, prodrugs, tautomers or physiologically tolerated acid addition salts thereof for the treatment of a medical disorder susceptible to the treatment with a 5-$HT_6$ receptor ligand.

The invention furthermore relates to a pharmaceutical composition comprising at least one compound of formula IA and/or IB, a stereoisomer, N-oxide, prodrug, tautomer and/or physiologically tolerated acid addition salt thereof or at least one compound of formula IA and/or IB, wherein at least one of the atoms has been replaced by its stable, non-radioactive isotope, and at least one physiologically acceptable carrier and/or auxiliary substance.

The invention relates moreover to the use of compounds of formula IA and/or IB or of a stereoisomer, N-oxide, prodrug, tautomer or physiologically tolerated acid addition salt thereof or of a compound of formula IA and/or IB, wherein at least one of the atoms has been replaced by its stable, non-radioactive isotope, for the preparation of a medicament for the treatment of a medical disorder susceptible to the treatment with a 5-$HT_6$ receptor ligand, and to a method for treating a medical disorder susceptible to the treatment with a 5-$HT_6$ receptor ligand, said method comprising administering an effective amount of at least one compound of formula IA and/or IB or of a stereoisomer, N-oxide, prodrug, tautomer or physiologically tolerated acid addition salt thereof or of a compound of formula IA and/or IB, wherein at least one of the atoms has been replaced by its stable, non-radioactive isotope, or of a pharmaceutical composition as defined above to a subject in need thereof.

The present invention also relates to the compounds of formula IA or IB or a stereoisomer, N-oxide, prodrug, tautomer or physiologically tolerated acid addition salt thereof or a compound of formula IA or IB, wherein at least one of the atoms has been replaced by its stable, non-radioactive isotope, for use in modulating the 5-$HT_6$ receptor.

DETAILED DESCRIPTION OF THE INVENTION

The disorders and diseases which are susceptible to treatment with a compound of the formula IA or IB include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, drug addiction and obesity.

Provided the compounds of the formula IA or IB of a given constitution may exist in different spatial arrangements, for example if they possess one or more centers of asymmetry, polysubstituted rings or double bonds, or as different tautomers, the invention also relates to enantiomeric mixtures, in particular racemates, diastereomeric mixtures and tautomeric mixtures, preferably, however, the respective essentially pure enantiomers (enantiomerically pure), diastereomers and tautomers of the compounds of formula I and/or of their salts and/or their N-oxides.

Particularly, the carbon atom of the nitrogen-containing ring (pyrrolidine (if $G^1$ and $G^2$ are $CH_2$), piperidine (if one of $G^1$ and $G^2$ is $CH_2$ and the other is $CH_2CH_2$) or azepane (if $G^1$ and $G^2$ are $CH_2CH_2$) carrying the phenyl group may have (S) or (R) configuration (except for the case that in compounds IA $G^1$ is $CH_2CH_2$, $G^2$ is $CH_2$ and $R^2$ is hydrogen; then said carbon atom is not asymmetric).

In the terms of the present invention, "prodrugs" are compounds which are metabolized in vivo to give the compounds of the invention of formula IA or IB. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula IA or IB wherein an external nitrogen atom, for example the nitrogen ring atom carrying the radical $R^1$ or a nitrogen atom of a primary or secondary amino group being a substituent $R^5$ (=$R^5$ is NH—C(O)—$NR^8R^9$, $NR^8R^9$, $NR^8R^9$—$C_1$-$C_6$-alkylene, O—$NR^8R^9$, $R^{10}$—CO—$NR^8$—$C_1$-$C_6$-alkylene, or a heterocycling ring containing a heteroatom-containing group $NR^{11}$ as ring member, wherein at least one of $R^8$ and $R^9$, or of $R^8$ and $R^{10}$, or $R^{11}$ is H), forms an amide/peptide bond in that this nitrogen atom is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an aminoacid group bonded via CO, e.g. glycine, alanine, serine, phenylalanine and the like bonded via CO. Suitable prodrugs are furthermore alkylcarbonyloxyalkylcarbamates, wherein said nitrogen atom carries a group —C(=O)—O—CHR$^x$—O—C(=O)—R$^y$, wherein R$^x$ and R$^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322. These groups can be removed under metabolic conditions and result in compounds of formula IA or IB, wherein said nitrogen atom carries a hydrogen atom instead.

The invention also relates to physiologically tolerated salts of the compounds of the formula IA or IB, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The invention also relates to N-oxides of the compounds of the formula IA or IB, provided that those compounds contain a basic nitrogen atom, such as the nitrogen atom of the heterocyclic moiety.

The organic moieties mentioned in the above definitions of the variables are—like the term halogen—collective terms for individual listings of the individual group members. The prefix $C_n$-$C_m$ indicates in each case the possible number of carbon atoms in the group.

In the terms of the present invention, halogen is fluorine, chlorine, bromine or iodine, preferably fluorine or chlorine.

$C_1$-$C_2$-Alkyl is methyl or ethyl.

$C_1$-$C_3$-alkyl is methyl, ethyl, n-propyl or isopropyl.

$C_1$-$C_4$-Alkyl is a straight-chain or branched alkyl group having from 1 to 4 carbon atoms. Examples are methyl, ethyl, n-propyl, iso-propyl, n-butyl, 2-butyl, iso-butyl or tert-butyl.

$C_1$-$C_6$-Alkyl is a straight-chain or branched alkyl group having from 1 to 6 carbon atoms. Examples include $C_1$-$C_4$-alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_2$ alkyl is an alkyl group having 1 or 2 carbon atoms, wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, or pentafluoroethyl.

Fluorinated $C_1$-$C_6$ alkyl is a straight-chain or branched alkyl group having from 1 to 6, especially 1 to 4 carbon atoms (=fluorinated $C_1$-$C_4$ alkyl), in particular 1 to 3 carbon atoms (=fluorinated $C_1$-$C_3$ alkyl), wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

$C_1$-$C_2$-Alkoxy is methoxy or ethoxy.

$C_1$-$C_3$-Alkoxy is methoxy, ethoxy, n-propoxy or isopropoxy.

$C_1$-$C_6$-Alkoxy is a straight-chain or branched alkyl group having from 1 to 6, in particular 1 to 4 carbon atoms (=$C_1$-$C_4$ alkoxy), which is bound to the remainder of the molecule via an oxygen atom. Examples include methoxy, ethoxy, n-propoxy, isopropoxy, n-butoxy, 2-butoxy, iso-butoxy, tert-butoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Fluorinated $C_1$-$C_2$-alkoxy is an alkoxy group having from 1 or 2 carbon atoms, wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, or pentafluoroethoxy.

Fluorinated $C_1$-$C_6$-alkoxy is a straight-chain or branched alkoxy group having from 1 to 6, in particular 1 to 4 carbon atoms (=fluorinated $C_1$-$C_4$-alkoxy), wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_6$-Hydroxyalkyl is a straight-chain or branched alkyl group having from 1 to 6, especially 1 to 4 carbon atoms (=$C_1$-$C_4$-hydroxyalkyl), in particular 1 to 3 carbon atoms (=$C_1$-$C_3$-hydroxyalkyl), wherein one of the hydrogen atoms is replaced by a hydroxy group, such as in 2-hydroxyethyl or 3-hydroxypropyl.

$C_1$-$C_6$-Alkoxy-$C_1$-$C_6$-alkyl is a straight-chain or branched alkyl group having from 1 to 6, especially 1 to 4 carbon atoms (=$C_1$-$C_6$-alkoxy-$C_1$-$C_4$-alkyl), in particular 1 to 3 carbon atoms (=$C_1$-$C_6$-alkoxy-$C_1$-$C_3$-alkyl), wherein one of the hydrogen atoms is replaced by a $C_1$-$C_6$-alkoxy group, such as in methoxymethyl, 1-methoxyethyl, 2-methoxyethyl, ethoxymethyl, 1-methoxypropyl, 2-methoxypropyl, 3-methoxypropyl, 1-ethoxypropyl, 2-ethoxypropyl, 3-ethoxypropyl and the like.

Fluorinated $C_1$-$C_6$-alkoxy-$C_1$-$C_6$-alkyl is a straight-chain or branched alkyl group having from 1 to 6, especially 1 to 4 carbon atoms (=fluorinated $C_1$-$C_6$-alkoxy-$C_1$-$C_4$-alkyl), in particular 1 to 3 carbon atoms (=fluorinated $C_1$-$C_6$-alkoxy-$C_1$-$C_3$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by a fluorine atoms, such as in difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

$C_1$-$C_6$-Alkoxy-$C_1$-$C_6$-alkoxy is a straight-chain or branched alkoxy group having from 1 to 6, especially 1 to 4 carbon atoms (=$C_1$-$C_6$-alkoxy-$C_1$-$C_4$-alkoxy), in particular 1 to 3 carbon atoms (=$C_1$-$C_6$-alkoxy-$C_1$-$C_3$-alkoxy), wherein one of the hydrogen atoms is replaced by a $C_1$-$C_6$-alkoxy group, such as in methoxymethoxy, 1-methoxyethoxy, 2-methoxyethoxy, ethoxymethoxy, 1-ethoxyethoxy, 2-ethoxyethoxy, 1-methoxypropoxy, 2-methoxypropoxy, 3-methoxypropoxy, 1-ethoxypropoxy, 2-ethoxypropoxy, 3-ethoxypropoxy and the like.

Fluorinated $C_1$-$C_6$-alkoxy-$C_1$-$C_6$-alkoxy is a straight-chain or branched alkoxy group having from 1 to 6, especially 1 to 4 carbon atoms (=fluorinated $C_1$-$C_6$-alkoxy-$C_1$-$C_4$-alkoxy), in particular 1 to 3 carbon atoms (=fluorinated $C_1$-$C_6$-alkoxy-$C_1$-$C_3$-alkoxy), wherein one of the hydrogen atoms is replaced by a $C_1$-$C_6$-alkoxy group and wherein at least one, e.g. 1, 2, 3, 4 or all of the remaining hydrogen atoms (either in the external alkoxy moiety or in the internal alkyleneoxy moiety or in both) are replaced by a fluorine atoms, such as in difluoromethoxymethoxy ($CHF_2OCH_2O$), trifluoromethoxymethoxy, 2-difluoromethoxyethoxy, 2-trifluoromethoxyethoxy, difluoro-methoxy-methoxy ($CH_3OCF_2O$), 1,1-difluoro-2-methoxyethyl, 2,2-difluoro-2-methoxyethyl and the like.

$C_1$-$C_6$-Alkylcarbonyl is a straight-chain or branched alkyl group having from 1 to 6, especially 1 to 4 carbon atoms (=$C_1$-$C_4$-alkylcarbonyl), in particular 1 to 3 carbon atoms (=$C_1$-$C_3$-alkylcarbonyl), which is bound via a carbonyl group (CO), such as in acetyl(methylcarbonyl) and propionyl (ethylcarbonyl).

Fluorinated $C_1$-$C_6$-alkylcarbonyl is a straight-chain or branched alkyl group having from 1 to 6, especially 1 to 4 carbon atoms (=fluorinated $C_1$-$C_4$-alkylcarbonyl), in particular 1 to 3 carbon atoms (=fluorinated $C_1$-$C_3$-alkylcarbonyl), which is bound via a carbonyl group (CO) and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_6$-Alkoxycarbonyl is a group R—O—C(O)—, wherein R is a straight-chain or branched alkyl group having from 1 to 6, especially 1 to 4 carbon atoms (=$C_1$-$C_4$ alkoxycarbonyl), in particular 1 to 3 carbon atoms (=$C_1$-$C_3$ alkoxycarbonyl), such as methoxycarbonyl, ethoxycarbonyl, propoxycarbony, isopropoxycarbonyl, butoxycarbonyl and the like.

$C_1$-$C_6$-Alkylcarbonylamino is a straight-chain or branched alkyl group having from 1 to 6, especially 1 to 4 carbon atoms (=$C_1$-$C_4$ alkylcarbonylamino), in particular 1 to 3 carbon atoms (=$C_1$-$C_4$ alkylcarbonylamino), which is bound via a carbonylamino group (CO—NH—), such as in acetamido (acetylamino) ($CH_3CONH$—) and propionamido ($CH_3CH_2CONH$—).

Fluorinated $C_1$-$C_6$-alkylcarbonylamino is a straight-chain or branched alkyl group having from 1 to 6, especially 1 to 4 carbon atoms (=fluorinated $C_1$-$C_4$ alkylcarbonylamino), in particular 1 to 3 carbon atoms (=fluorinated $C_1$-$C_4$ alkylcarbonylamino), which is bound via a carbonylamino group (CO—NH—) and wherein at least one of the remaining hydrogen atoms, e.g. 1, 2, 3, or 4 of the hydrogen atoms are replaced by a fluorine atom, such as in trifluoroacetylamino and 3,3,3-trifluoropropionylamino.

$C_1$-$C_6$-Alkylthio (also termed as $C_1$-$C_6$-alkylsulfanyl) (or $C_1$-$C_6$-alkylsulfinyl or $C_1$-$C_6$-alkylsulfonyl, respectively) refer to straight-chain or branched alkyl groups having 1 to 6 carbon atoms, e.g. 1 to 4 carbon atoms, which are bound to the remainder of the molecule via a sulfur atom (or S(O) in case of alkylsulfinyl or S(O)$_2$ in case of alkylsulfonyl, respectively), at any bond in the alkyl group. Examples for $C_1$-$C_4$-alkylthio include methylthio, ethylthio, propylthio, isopropylthio, and n-butylthio. Examples for $C_1$-$C_4$-alkylsulfinyl include methylsulfinyl, ethylsulfinyl, propylsulfinyl, isopropylsulfinyl, and n-butylsulfinyl. Examples for $C_1$-$C_4$-alkylsulfonyl include methylsulfonyl, ethylsulfonyl, propylsulfonyl, isopropylsulfonyl, and n-butylsulfonyl.

Fluorinated $C_1$-$C_6$-alkylthio (also termed fluorinated $C_1$-$C_6$-alkylsulfanyl) is a straight-chain or branched alkylthio group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$-alkylsulfinyl is a straight-chain or branched alkylsulfinyl group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$-alkylsulfonyl is a straight-chain or branched alkylsulfonyl group having from 1 to 6, in particular 1 to 4 carbon atoms, wherein at least one, e.g. 1, 2, 3, 4 or all of the hydrogen atoms are replaced by fluorine atoms.

$C_3$-$C_6$-Cycloalkyl is a cycloaliphatic radical having from 3 to 6 C atoms, such as cyclopropyl, cyclobutyl, cyclopentyl and cyclohexyl.

Fluorinated $C_3$-$C_6$-cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl (2-methylprop-2-en-1-yl) and the like. $C_3$-$C_6$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_1$-$C_2$-Alkylene is a hydrocarbon bridging group having 1 or 2 carbon atoms. Examples are methylene (—$CH_2$—), 1,1-ethylene (—CH($CH_3$)—) and 1,2-ethylene (—$CH_2CH_2$—).

$C_2$-$C_3$-Alkylene is a hydrocarbon bridging group having 2 or 3 carbon atoms. Examples are 1,1-ethylene (—CH($CH_3$)—), 1,2-ethylene (—$CH_2CH_2$—), 1,1-propylene (—CH($CH_2CH_3$)—), 1,2-propylene (—$CH_2$—CH($CH_3$)— or —CH($CH_3$)—$CH_2$—) and 1,3-propylene (—$CH_2CH_2CH_2$—).

$C_1$-$C_4$-Alkylene is a hydrocarbon bridging group having 1, 2, 3 or 4 carbon atoms, like methylene, 1,1-ethylene, 1,2-ethylene, 1,1-propylene, 1,2-propylene, 1,3-propylene, 1,4-butylene (—$CH_2CH_2CH_2CH_2$—) and the like.

$C_1$-$C_6$-Alkylene is a hydrocarbon bridging group having 1, 2, 3, 4, 5 or 6 carbon atoms, like methylene, 1,1-ethylene, 1,2-ethylene, 1,2- and 1,3-propylene, 1,4-butylene, 1,5-pentylene, 1,6-hexylene (hexamethylene) and the like.

Fluorinated $C_1$-$C_6$-alkylene is a hydrocarbon bridging group having 1, 2, 3, 4, 5 or 6 carbon atoms, wherein at least one, e.g. 1, 2, 3, 4 or all of the hydrogen atoms are replaced by a fluorine atoms, like fluoromethylene, difluoromethylene 1-fluoro-1,1-ethylene, 2-fluoro-1,1-ethylene, 1,2-difluoro-1,1-ethylene, 2,2-difluoro-1,1-ethylene, 2,2,2-trifluoro-1,1-ethylene, 1-fluoro-1,2-ethylene, 2-fluoro-1,2-ethylene, 1,1-difluoro-1,2-ethylene, 1,2-difluoro-1,2-ethylene, and the like.

If $R^8$ and $R^9$ form together with N a 4-, 5- or 6-membered ring, examples for this type of radical comprise 1-azetidinyl, 1-azetinyl, 1-pyrrolinyl, 1-pyrrolidinyl, 1-pyrazolinyl, 1-pyrazolidinyl, 1-imidazolinyl, 1-imidazolidinyl, 3-oxazolinyl, 3-oxazolidinyl, 1-piperidinyl, 1-piperazinyl, 4-morpholinyl, 1-pyrrolyl, 1-pyrazolyl, 1-imidazolyl, 1-triazolyl and the like.

Examples for saturated or unsaturated 3-, 4-, 5-, 6- or 7-membered heterocyclic rings comprise saturated or unsaturated, aromatic or non-aromatic heterocyclic rings. Examples therefore include aziridyl, diaziridinyl, oxiranyl, azetidinyl, azetinyl, di- and tetrahydrofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl, pyridyl, pyrimidinyl, pyrazinyl, pyridazinyl, thienyl, furyl, pyrrolyl, oxazolyl, isoxazolyl, thiazolyl, isothiazolyl, pyrazolyl, imidazolyl, 1,3,4]oxadiazolyl, [1,2,3]oxadiazolyl, [1,2,4]oxadiazolyl, [1,3,4]thiadiazolyl, [1,3,4]thiadiazolyl, [1,2,3]thiadiazolyl, [1,2,4]thiadiazolyl 1H-, 2H- or 3H-1,2,3-triazol-4-yl, 2H-triazol-3-yl, 1H-, 2H-, or 4H-1,2,4-triazolyl, 1H- or 2H-tetrazolyl and the like.

The remarks made above and in the following with respect to preferred aspects of the invention, e.g. to preferred meanings of the variables A, B, $X^1$, $X^2$, $G^1$, $G^2$, $R^1$, $R^2$, $R^3$, $R^4$, $R^5$, $R^6$, $R^7$, $R^8$, $R^9$, $R^{10}$, $R^{11}$, o and p of compounds IA and IB, to preferred compounds IA and IB and to preferred embodiments of the method or the use according to the invention, apply in each case on their own or in particular to combinations thereof.

Among compounds IA and IB, preference is given to compounds IA.

In one preferred embodiment of the invention, $X^1$ is $NR^4$. In an alternatively preferred embodiment, $X^1$ is a bond. More preferably, $X^1$ is $NR^4$. In this case, $R^4$ has one of the above given general meanings or is preferably hydrogen or $C_1$-$C_4$-alkyl and more preferably hydrogen or methyl and specifically hydrogen.

In one preferred embodiment of the invention, $X^2$ is $NR^4$. In an alternatively preferred embodiment, $X^2$ is a bond. More preferably, $X^2$ is $NR^4$. In this case, $R^4$ has one of the above given general meanings or is preferably hydrogen or $C_1$-$C_4$-alkyl and more preferably hydrogen or methyl and specifically hydrogen.

In one preferred embodiment of the invention $X^1$ and $X^2$ are $NR^4$. In this case, $R^4$ has one of the above given general meanings or is preferably hydrogen or $C_1$-$C_4$-alkyl and more preferably hydrogen or methyl and specifically hydrogen.

Preferably, $R^1$ is hydrogen, $C_1$-$C_3$-alkyl or fluorinated $C_1$-$C_3$-alkyl, more preferably hydrogen, methyl, ethyl or 2-fluoroethyl, even more preferably hydrogen, methyl or ethyl and in particular hydrogen or methyl.

The radical $R^2$ replaces one hydrogen atom of the carbon ring atoms of the N-containing ring to which it is bound; also of the groups $G^1$ and $G^2$.

$R^2$ is preferably bound in α-position to the nitrogen ring atom.

$R^2$ is preferably hydrogen or methyl and more preferably hydrogen.

$R^3$ is preferably selected from hydrogen, $C_1$-$C_4$-alkyl, fluorinated $C_1$-$C_4$-alkyl, $C_1$-$C_4$-alkoxy and fluorinated $C_1$-$C_4$-alkoxy, more preferably from hydrogen, $C_1$-$C_4$-alkyl and $C_1$-$C_4$-alkoxy, even more preferably from methoxy, ethoxy, methyl and ethyl, in particular from methoxy, ethoxy and methyl, and is specifically methoxy.

$R^4$ is preferably hydrogen or $C_1$-$C_4$-alkyl, more preferably hydrogen or methyl and is specifically hydrogen.

In a specific embodiment, $R^5$ is not halogen.

$R^5$ is preferably selected from $C_1$-$C_6$-hydroxyalkyl, $C_1$-$C_6$-alkoxy, $C_1$-$C_6$-hydroxyalkoxy, $C_1$-$C_6$-alkoxy-$C_1$-$C_6$-alkoxy, fluorinated $C_1$-$C_6$-alkoxy, fluorinated $C_1$-$C_6$-alkoxy-$C_1$-$C_6$-alkoxy and a group -A-[O—B]$_p$—O—$R^7$. More preferably, $R^5$ is selected from fluorinated $C_1$-$C_6$-alkoxy and a group -A-[O—B]$_p$—O—$R^7$ and even more preferably from fluorinated $C_1$-$C_2$-alkoxy and a group -A-[O—B]$_p$—O—$R^7$.

In a specific embodiment, $R^5$ is not $OCF_3$.

In the group A-[O—B]$_p$—O—$R^7$, A is preferably $C_1$-$C_2$-alkylene, more preferably methylene ($CH_2$) or 1,1-ethylene [CH($CH_3$)].

In the group A-[O—B]$_p$—O—$R^7$, B is preferably $C_2$-$C_3$-alkylene, more preferably 1,2-ethylene or 1,2-propylene.

p is preferably 0.

$R^7$ is preferably $C_1$-$C_2$-alkyl or fluorinated $C_1$-$C_2$-alkyl.

Thus, the group A-[O—B]$_p$—O—$R^7$ is preferably selected from $C_1$-$C_2$-alkoxy-$C_1$-$C_2$-alkyl and (fluorinated $C_1$-$C_2$-alkoxy)-$C_1$-$C_2$-alkyl.

Very preferably, $R^5$ is selected from fluorinated $C_1$-$C_2$-alkoxy, $C_1$-$C_2$-alkoxy-$C_1$-$C_2$-alkyl and (fluorinated $C_1$-$C_2$-alkoxy)-$C_1$-$C_2$-alkyl, even more preferably from fluorinated $C_1$-$C_2$-alkoxy, $C_1$-$C_2$-alkoxy-methyl, 1-($C_1$-$C_2$-alkoxy)-ethyl, (fluorinated $C_1$-$C_2$-alkoxy)-methyl and 1-(fluorinated $C_1$-$C_2$-alkoxy)-ethyl and particularly preferably from difluoro-methoxy, trifluoromethoxy, methoxymethyl, ethoxymethyl, 2,2,2-trifluoroethoxymethyl and 1-methoxyethyl. In particular, $R^5$ is selected from difluoromethoxy, methoxymethyl, ethoxymethyl, 2,2,2-trifluoroethoxymethyl and 1-methoxyethyl, and is specifically di-fluoromethoxy or methoxymethyl. Very specifically, $R^5$ is difluoromethoxy.

Preferably, $R^5$ is bound in the 2- or 3-position, more preferably in the 2-position, relative to the 1-position of the sulfonyl group $SO_2$—$X^1$ or $SO_2$—$X^2$.

$R^6$ is preferably selected from F, Cl, methyl, difluoromethyl, trifluoromethyl, methoxy, difluoromethoxy and trifluoromethoxy and is more preferably methyl.

o is preferably 0 or 1. In case $R^5$ is fluorinated $C_1$-$C_2$-alkoxy, o is specifically 1 and in case $R^5$ is a group A—[O—B—]$_p$—O—$R^7$, o is specifically 0.

In case o is 1 and $R^5$ is bound in the 2- or 3-position, $R^6$ is preferably bound in the 5-position, relative to the 1-position of the sulfonyl group $SO_2$—$X^1$ or $SO_2$—$X^2$ and to the 2- or 3-position of $R^5$. If o is 1 and $R^5$ is bound in the 2-position, $R^6$ may preferably also be bound in the 4-position, relative to the 1-position of the sulfonyl group $SO_2$—$X^1$ or $SO_2$—$X^2$ and to the 2-position of $R^5$. But more preferably, if o is 1 and $R^5$ is bound in the 2-position, $R^6$ is preferably bound in the 5-position, relative to the 1-position of the sulfonyl group $SO_2$—$X^1$ or $SO_2$—$X^2$ and to the 2-position of $R^5$.

Preferably, at most one of $G^1$ and $G^2$ is $CH_2CH_2$. More preferably, $G^1$ is $CH_2$ and $G^2$ is $CH_2$ (the N-containing ring thus resulting in a pyrrolidine-3-yl ring); or $G^1$ is $CH_2$ and $G^2$ is $CH_2CH_2$ (the N-containing ring thus resulting in a piperidine-3-yl ring); or $G^1$ is $CH_2CH_2$ and $G^2$ is $CH_2$ (the N-containing ring thus resulting in a piperidine-4-yl ring). Specifically, $G^1$ is $CH_2$ and $G^2$ is $CH_2$ (the N-containing ring thus resulting in a pyrrolidine-3-yl ring) or $G^1$ is $CH_2CH_2$ and $G^2$ is $CH_2$ (the N-containing ring thus resulting in a piperidine-4-yl ring).

The invention specifically relates to compounds of formula IA or IB, preferably IA, the stereoisomers, N-oxides, prodrugs, tautomers and/or physiologically tolerated acid addition salts thereof, wherein $X^1$ and $X^2$ are NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ and $X^2$ are NH;
$R^1$ is methyl;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ and $X^2$ are NH;
$R^1$ is hydrogen;
$R^2$ is hydrogen;
$R^3$ is methoxy;
$R^5$ is 2-methoxymethyl, relative to the 1-position of the sulfonylamino group $SO_2$—NH;
$G^1$ is $CH_2$;
$G^2$ is $CH_2$; and
o is 0;
or
$X^1$ and $X^2$ are NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2CH_2$; and
o is 1;
or
$X^1$ and $X^2$ are NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2CH_2$;
$G^1$ is $CH_2$; and
o is 1;
or
$X^1$ and $X^2$ are NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ and $X^2$ are NH;
$R^1$ is methyl;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ and $X^2$ are NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2$;
$G^2$ is $CH_2CH_2$; and
o is 1;
or
$X^1$ and $X^2$ are NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;

R⁶ is 4-methyl, relative to the 1-position of the sulfonylamino group SO₂—NH and to the 2-position of 2-difluoromethoxy as radical R⁵;
G¹ is CH₂CH₂;
G¹ is CH₂; and
o is 1;
or
X¹ and X² are NH;
R¹ is hydrogen;
R² is hydrogen;
R³ is ethoxy;
R⁵ is 2-difluoromethoxy, relative to the 1-position of the sulfonylamino group SO₂—NH;
R⁶ is 5-methyl, relative to the 1-position of the sulfonylamino group SO₂—NH and to the 2-position of 2-difluoromethoxy as radical R⁵;
G¹ is CH₂;
G² is CH₂; and
o is 1;
or
X¹ and X² are NH;
R¹ is methyl;
R² is hydrogen;
R³ is ethoxy;
R⁵ is 2-difluoromethoxy, relative to the 1-position of the sulfonylamino group SO₂—NH;
R⁶ is 5-methyl, relative to the 1-position of the sulfonylamino group SO₂—NH and to the 2-position of 2-difluoromethoxy as radical R⁵;
G¹ is CH₂;
G² is CH₂; and
o is 1;
or
X¹ and X² are NH;
R¹ is hydrogen;
R² is hydrogen;
R³ is ethoxy;
R⁵ is 2-methoxymethyl, relative to the 1-position of the sulfonylamino group SO₂—NH;
G¹ is CH₂;
G² is CH₂; and
o is 0;
or
X¹ and X² are NH;
R¹ is hydrogen;
R² is hydrogen;
R³ is ethoxy;
R⁵ is 2-difluoromethoxy, relative to the 1-position of the sulfonylamino group SO₂—NH;
R⁶ is 5-methyl, relative to the 1-position of the sulfonylamino group SO₂—NH and to the 2-position of 2-difluoromethoxy as radical R⁵;
G¹ is CH₂CH₂;
G¹ is CH₂; and
o is 1;
or
X¹ and X² are NH;
R¹ is hydrogen;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵;
G¹ is CH₂;
G² is CH₂; and
o is 1;
or
X¹ and X² are NH;
R¹ is methyl;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵;
G¹ is CH₂;
G² is CH₂; and
o is 1;
or
X¹ and X² are NH;
R¹ is hydrogen;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵;
G¹ is CH₂;
G² is CH₂CH₂; and
o is 1;
or
X¹ and X² are NH;
R¹ is hydrogen;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵;
G¹ is CH₂CH₂;
G¹ is CH₂; and
o is 1;
or
X¹ and X² are NH;
R¹ is hydrogen;
R² is hydrogen;
R³ is methoxy;
R⁵ is 2-methoxymethyl, relative to the 1-position of the sulfonylamino group SO₂—NH;
G¹ is CH₂CH₂;
G² is CH₂; and
o is 0;
or
X¹ and X² are NH;
R¹ is methyl;
R² is hydrogen;

R³ is methoxy;
R⁵ is 2-difluoromethoxy, relative to the 1-position of the sulfonylamino group SO₂—NH;
R⁶ is 5-methyl, relative to the 1-position of the sulfonylamino group SO₂—NH and to the 2-position of 2-difluoromethoxy as radical R⁵;
G¹ is CH₂CH₂;
G² is CH₂; and
o is 1;

the first three, the fifth, the ninth and the last two compounds being particularly preferred.

Among the above listed compounds, compounds of formula IA are preferred.

Examples of preferred compounds are compounds of the following formulae I.a to I.r, where the variables have one of the general or preferred meanings given above. Examples of preferred compounds which are represented by the formulae I.a to I.r are the individual compounds, where the variables R¹, R³, R⁵ and (R⁶)$_o$ have the meanings given in one row of table A. Moreover, the meanings mentioned for the individual variables in table A are per se, independently of the combination in which they are mentioned, a particularly preferred embodiment of the substituents in question.

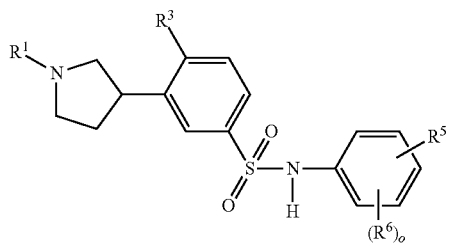
I.a

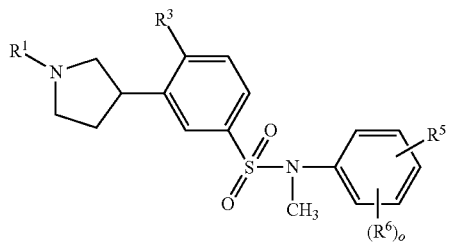
I.b

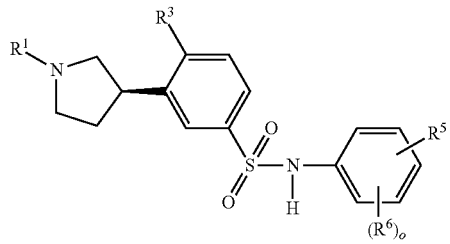
I.c

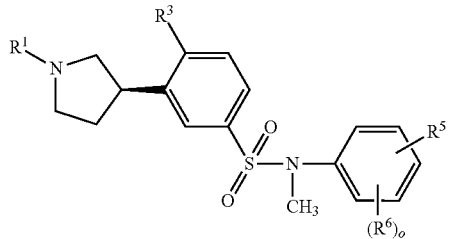
I.d

-continued

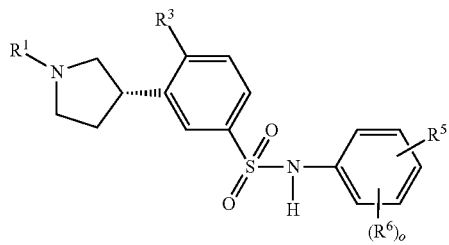
I.e

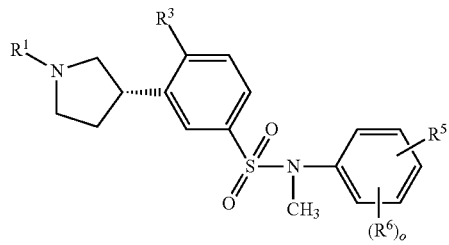
I.f

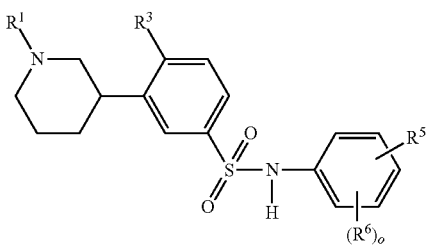
I.g

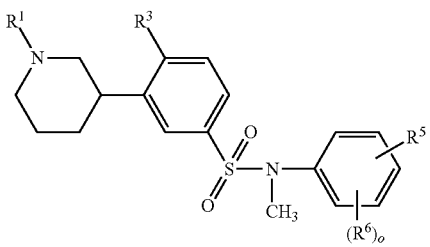
I.h

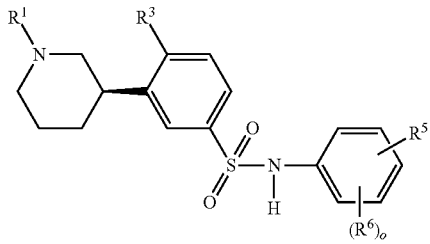
I.i

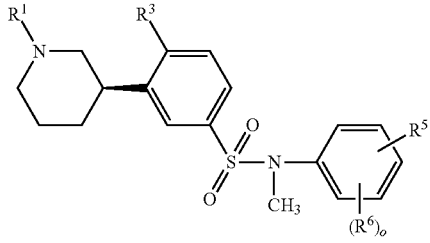
I.j

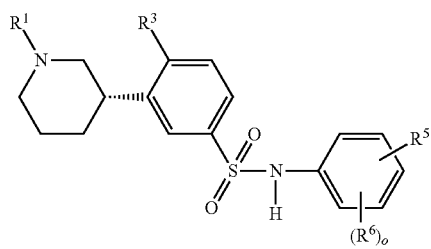

I.k

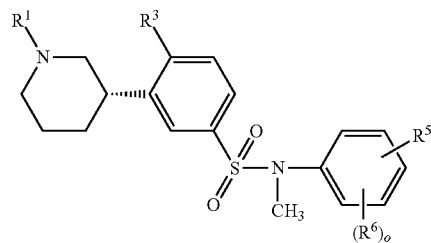

I.l

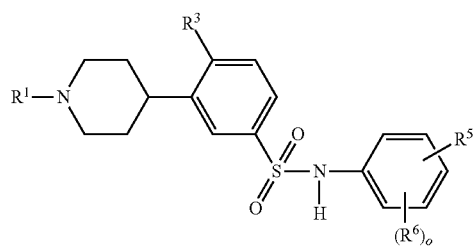

I.m

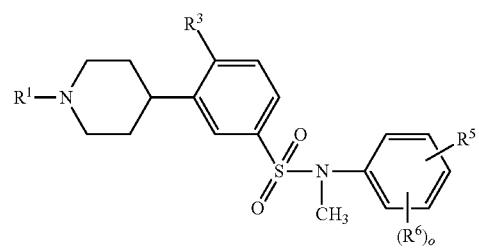

I.n

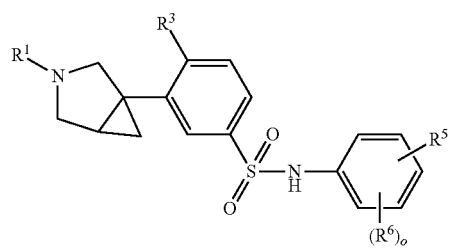

I.o

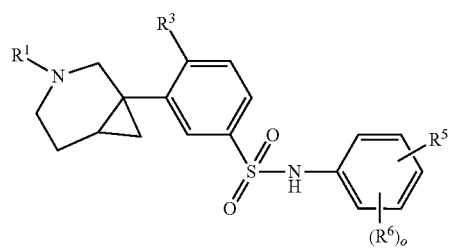

I.p

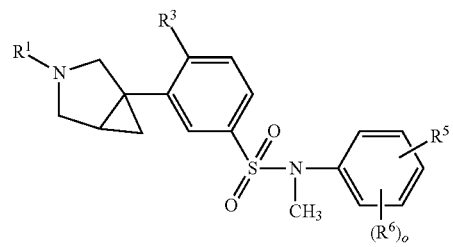

I.q

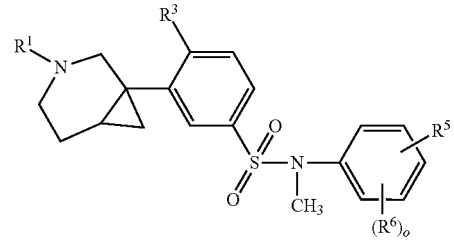

I.r

In table A, the position of the radical $R^5$ and, if present, $R^6$ is defined as follows:

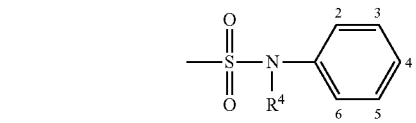

TABLE A

| No. | $R^1$ | $R^3$ | $R^5$ | $(R^6)_o$ |
|---|---|---|---|---|
| A-1 | H | methoxy | 2-OCHF$_2$ | — |
| A-2 | H | methoxy | 3-OCHF$_2$ | — |
| A-3 | H | methoxy | 4-OCHF$_2$ | — |
| A-4 | H | methoxy | 2-OCF$_3$ | — |
| A-5 | H | methoxy | 3-OCF$_3$ | — |
| A-6 | H | methoxy | 4-OCF$_3$ | — |
| A-7 | H | methoxy | 2-CF$_3$ | — |
| A-8 | H | methoxy | 3-CF$_3$ | — |
| A-9 | H | methoxy | 4-CF$_3$ | — |
| A-10 | H | methoxy | 2-CH$_2$OCH$_3$ | — |
| A-11 | H | methoxy | 3-CH$_2$OCH$_3$ | — |
| A-12 | H | methoxy | 4-CH$_2$OCH$_3$ | — |
| A-13 | H | methoxy | 2-CH$_2$OCH$_2$CH$_3$ | — |
| A-14 | H | methoxy | 3-CH$_2$OCH$_2$CH$_3$ | — |
| A-15 | H | methoxy | 4-CH$_2$OCH$_2$CH$_3$ | — |
| A-16 | H | methoxy | 2-CH$_2$OCF$_3$ | — |
| A-17 | H | methoxy | 3-CH$_2$OCF$_3$ | — |
| A-18 | H | methoxy | 4-CH$_2$OCF$_3$ | — |
| A-19 | H | methoxy | 2-CH$_2$OCH$_2$CF$_3$ | — |
| A-20 | H | methoxy | 3-CH$_2$OCH$_2$CF$_3$ | — |
| A-21 | H | methoxy | 4-CH$_2$OCH$_2$CF$_3$ | — |
| A-22 | H | methoxy | 2-CH(CH$_3$)OCH$_3$ | — |
| A-23 | H | methoxy | 3-CH(CH$_3$)OCH$_3$ | — |
| A-24 | H | methoxy | 4-CH(CH$_3$)OCH$_3$ | — |
| A-25 | H | methoxy | 2-CH(CH$_3$)OCH$_2$CH$_3$ | — |
| A-26 | H | methoxy | 3-CH(CH$_3$)OCH$_2$CH$_3$ | — |
| A-27 | H | methoxy | 4-CH(CH$_3$)OCH$_2$CH$_3$ | — |
| A-28 | H | methoxy | 2-CH(CH$_3$)OCF$_3$ | — |
| A-29 | H | methoxy | 3-CH(CH$_3$)OCF$_3$ | — |
| A-30 | H | methoxy | 4-CH(CH$_3$)OCF$_3$ | — |
| A-31 | H | methoxy | 2-CH(CH$_3$)OCH$_2$CF$_3$ | — |
| A-32 | H | methoxy | 3-CH(CH$_3$)OCH$_2$CF$_3$ | — |
| A-33 | H | methoxy | 4-CH(CH$_3$)OCH$_2$CF$_3$ | — |
| A-34 | H | methoxy | 2-OCHF$_2$ | 3-methyl |
| A-35 | H | methoxy | 2-OCHF$_2$ | 4-methyl |
| A-36 | H | methoxy | 2-OCHF$_2$ | 5-methyl |

TABLE A-continued

| No. | $R^1$ | $R^3$ | $R^5$ | $(R^6)_o$ |
|---|---|---|---|---|
| A-37 | H | methoxy | 2-OCHF$_2$ | 6-methyl |
| A-38 | H | methoxy | 3-OCHF$_2$ | 2-methyl |
| A-39 | H | methoxy | 3-OCHF$_2$ | 4-methyl |
| A-40 | H | methoxy | 3-OCHF$_2$ | 5-methyl |
| A-41 | H | methoxy | 3-OCHF$_2$ | 6-methyl |
| A-42 | H | methoxy | 2-OCHF$_2$ | 3-F |
| A-43 | H | methoxy | 2-OCHF$_2$ | 4-F |
| A-44 | H | methoxy | 2-OCHF$_2$ | 5-F |
| A-45 | H | methoxy | 2-OCHF$_2$ | 6-F |
| A-46 | H | methoxy | 3-OCHF$_2$ | 2-F |
| A-47 | H | methoxy | 3-OCHF$_2$ | 4-F |
| A-48 | H | methoxy | 3-OCHF$_2$ | 5-F |
| A-49 | H | methoxy | 3-OCHF$_2$ | 6-F |
| A-50 | H | methoxy | 2-OCHF$_2$ | 3-Cl |
| A-51 | H | methoxy | 2-OCHF$_2$ | 4-Cl |
| A-52 | H | methoxy | 2-OCHF$_2$ | 5-Cl |
| A-53 | H | methoxy | 2-OCHF$_2$ | 6-Cl |
| A-54 | H | methoxy | 3-OCHF$_2$ | 2-Cl |
| A-55 | H | methoxy | 3-OCHF$_2$ | 4-Cl |
| A-56 | H | methoxy | 3-OCHF$_2$ | 5-Cl |
| A-57 | H | methoxy | 3-OCHF$_2$ | 6-Cl |
| A-58 | H | methoxy | 2-CH$_2$OCH$_3$ | 3-methyl |
| A-59 | H | methoxy | 2-CH$_2$OCH$_3$ | 4-methyl |
| A-60 | H | methoxy | 2-CH$_2$OCH$_3$ | 5-methyl |
| A-61 | H | methoxy | 2-CH$_2$OCH$_3$ | 6-methyl |
| A-62 | H | methoxy | 3-CH$_2$OCH$_3$ | 2-methyl |
| A-63 | H | methoxy | 3-CH$_2$OCH$_3$ | 4-methyl |
| A-64 | H | methoxy | 3-CH$_2$OCH$_3$ | 5-methyl |
| A-65 | H | methoxy | 3-CH$_2$OCH$_3$ | 6-methyl |
| A-66 | H | methoxy | 2-CH$_2$OCH$_3$ | 3-F |
| A-67 | H | methoxy | 2-CH$_2$OCH$_3$ | 4-F |
| A-68 | H | methoxy | 2-CH$_2$OCH$_3$ | 5-F |
| A-69 | H | methoxy | 2-CH$_2$OCH$_3$ | 6-F |
| A-70 | H | methoxy | 3-CH$_2$OCH$_3$ | 2-F |
| A-71 | H | methoxy | 3-CH$_2$OCH$_3$ | 4-F |
| A-72 | H | methoxy | 3-CH$_2$OCH$_3$ | 5-F |
| A-73 | H | methoxy | 3-CH$_2$OCH$_3$ | 6-F |
| A-74 | H | methoxy | 2-CH$_2$OCH$_3$ | 3-Cl |
| A-75 | H | methoxy | 2-CH$_2$OCH$_3$ | 4-Cl |
| A-76 | H | methoxy | 2-CH$_2$OCH$_3$ | 5-Cl |
| A-77 | H | methoxy | 2-CH$_2$OCH$_3$ | 6-Cl |
| A-78 | H | methoxy | 3-CH$_2$OCH$_3$ | 2-Cl |
| A-79 | H | methoxy | 3-CH$_2$OCH$_3$ | 4-Cl |
| A-80 | H | methoxy | 3-CH$_2$OCH$_3$ | 5-Cl |
| A-81 | H | methoxy | 3-CH$_2$OCH$_3$ | 6-Cl |
| A-82 | H | methoxy | 2-CF$_3$ | 3-F |
| A-83 | H | methoxy | 2-CF$_3$ | 4-F |
| A-84 | H | methoxy | 2-CF$_3$ | 5-F |
| A-85 | H | methoxy | 2-CF$_3$ | 6-F |
| A-86 | H | methoxy | 3-CF$_3$ | 2-F |
| A-87 | H | methoxy | 3-CF$_3$ | 4-F |
| A-88 | H | methoxy | 3-CF$_3$ | 5-F |
| A-89 | H | methoxy | 3-CF$_3$ | 6-F |
| A-90 | methyl | methoxy | 2-OCHF$_2$ | — |
| A-91 | methyl | methoxy | 3-OCHF$_2$ | — |
| A-92 | methyl | methoxy | 4-OCHF$_2$ | — |
| A-93 | methyl | methoxy | 2-OCF$_3$ | — |
| A-94 | methyl | methoxy | 3-OCF$_3$ | — |
| A-95 | methyl | methoxy | 4-OCF$_3$ | — |
| A-96 | methyl | methoxy | 2-CF$_3$ | — |
| A-97 | methyl | methoxy | 3-CF$_3$ | — |
| A-98 | methyl | methoxy | 4-CF$_3$ | — |
| A-99 | methyl | methoxy | 2-CH$_2$OCH$_3$ | — |
| A-100 | methyl | methoxy | 3-CH$_2$OCH$_3$ | — |
| A-101 | methyl | methoxy | 4-CH$_2$OCH$_3$ | — |
| A-102 | methyl | methoxy | 2-CH$_2$OCH$_2$CH$_3$ | — |
| A-103 | methyl | methoxy | 3-CH$_2$OCH$_2$CH$_3$ | — |
| A-104 | methyl | methoxy | 4-CH$_2$OCH$_2$CH$_3$ | — |
| A-105 | methyl | methoxy | 2-CH$_2$OCF$_3$ | — |
| A-106 | methyl | methoxy | 3-CH$_2$OCF$_3$ | — |
| A-107 | methyl | methoxy | 4-CH$_2$OCF$_3$ | — |
| A-108 | methyl | methoxy | 2-CH$_2$OCH$_2$CF$_3$ | — |
| A-109 | methyl | methoxy | 3-CH$_2$OCH$_2$CF$_3$ | — |
| A-110 | methyl | methoxy | 4-CH$_2$OCH$_2$CF$_3$ | — |
| A-111 | methyl | methoxy | 2-CH(CH$_3$)OCH$_3$ | — |
| A-112 | methyl | methoxy | 3-CH(CH$_3$)OCH$_3$ | — |
| A-113 | methyl | methoxy | 4-CH(CH$_3$)OCH$_3$ | — |
| A-114 | methyl | methoxy | 2-CH(CH$_3$)OCH$_2$CH$_3$ | — |
| A-115 | methyl | methoxy | 3-CH(CH$_3$)OCH$_2$CH$_3$ | — |
| A-116 | methyl | methoxy | 4-CH(CH$_3$)OCH$_2$CH$_3$ | — |
| A-117 | methyl | methoxy | 2-CH(CH$_3$)OCF$_3$ | — |
| A-118 | methyl | methoxy | 3-CH(CH$_3$)OCF$_3$ | — |
| A-119 | methyl | methoxy | 4-CH(CH$_3$)OCF$_3$ | — |
| A-120 | methyl | methoxy | 2-CH(CH$_3$)OCH$_2$CF$_3$ | — |
| A-121 | methyl | methoxy | 3-CH(CH$_3$)OCH$_2$CF$_3$ | — |
| A-122 | methyl | methoxy | 4-CH(CH$_3$)OCH$_2$CF$_3$ | — |
| A-123 | methyl | methoxy | 2-OCHF$_2$ | 3-methyl |
| A-124 | methyl | methoxy | 2-OCHF$_2$ | 4-methyl |
| A-125 | methyl | methoxy | 2-OCHF$_2$ | 5-methyl |
| A-126 | methyl | methoxy | 2-OCHF$_2$ | 6-methyl |
| A-127 | methyl | methoxy | 3-OCHF$_2$ | 2-methyl |
| A-128 | methyl | methoxy | 3-OCHF$_2$ | 4-methyl |
| A-129 | methyl | methoxy | 3-OCHF$_2$ | 5-methyl |
| A-130 | methyl | methoxy | 3-OCHF$_2$ | 6-methyl |
| A-131 | methyl | methoxy | 2-OCHF$_2$ | 3-F |
| A-132 | methyl | methoxy | 2-OCHF$_2$ | 4-F |
| A-133 | methyl | methoxy | 2-OCHF$_2$ | 5-F |
| A-134 | methyl | methoxy | 2-OCHF$_2$ | 6-F |
| A-135 | methyl | methoxy | 3-OCHF$_2$ | 2-F |
| A-136 | methyl | methoxy | 3-OCHF$_2$ | 4-F |
| A-137 | methyl | methoxy | 3-OCHF$_2$ | 5-F |
| A-138 | methyl | methoxy | 3-OCHF$_2$ | 6-F |
| A-139 | methyl | methoxy | 2-OCHF$_2$ | 3-Cl |
| A-140 | methyl | methoxy | 2-OCHF$_2$ | 4-Cl |
| A-141 | methyl | methoxy | 2-OCHF$_2$ | 5-Cl |
| A-142 | methyl | methoxy | 2-OCHF$_2$ | 6-Cl |
| A-143 | methyl | methoxy | 3-OCHF$_2$ | 2-Cl |
| A-144 | methyl | methoxy | 3-OCHF$_2$ | 4-Cl |
| A-145 | methyl | methoxy | 3-OCHF$_2$ | 5-Cl |
| A-146 | methyl | methoxy | 3-OCHF$_2$ | 6-Cl |
| A-147 | methyl | methoxy | 2-CH$_2$OCH$_3$ | 3-methyl |
| A-148 | methyl | methoxy | 2-CH$_2$OCH$_3$ | 4-methyl |
| A-149 | methyl | methoxy | 2-CH$_2$OCH$_3$ | 5-methyl |
| A-150 | methyl | methoxy | 2-CH$_2$OCH$_3$ | 6-methyl |
| A-151 | methyl | methoxy | 3-CH$_2$OCH$_3$ | 2-methyl |
| A-152 | methyl | methoxy | 3-CH$_2$OCH$_3$ | 4-methyl |
| A-153 | methyl | methoxy | 3-CH$_2$OCH$_3$ | 5-methyl |
| A-154 | methyl | methoxy | 3-CH$_2$OCH$_3$ | 6-methyl |
| A-155 | methyl | methoxy | 2-CH$_2$OCH$_3$ | 3-F |
| A-156 | methyl | methoxy | 2-CH$_2$OCH$_3$ | 4-F |
| A-157 | methyl | methoxy | 2-CH$_2$OCH$_3$ | 5-F |
| A-158 | methyl | methoxy | 2-CH$_2$OCH$_3$ | 6-F |
| A-159 | methyl | methoxy | 3-CH$_2$OCH$_3$ | 2-F |
| A-160 | methyl | methoxy | 3-CH$_2$OCH$_3$ | 4-F |
| A-161 | methyl | methoxy | 3-CH$_2$OCH$_3$ | 5-F |
| A-162 | methyl | methoxy | 3-CH$_2$OCH$_3$ | 6-F |
| A-163 | methyl | methoxy | 2-CH$_2$OCH$_3$ | 3-Cl |
| A-164 | methyl | methoxy | 2-CH$_2$OCH$_3$ | 4-Cl |
| A-165 | methyl | methoxy | 2-CH$_2$OCH$_3$ | 5-Cl |
| A-166 | methyl | methoxy | 2-CH$_2$OCH$_3$ | 6-Cl |
| A-167 | methyl | methoxy | 3-CH$_2$OCH$_3$ | 2-Cl |
| A-168 | methyl | methoxy | 3-CH$_2$OCH$_3$ | 4-Cl |
| A-169 | methyl | methoxy | 3-CH$_2$OCH$_3$ | 5-Cl |
| A-170 | methyl | methoxy | 3-CH$_2$OCH$_3$ | 6-Cl |
| A-171 | methyl | methoxy | 2-CF$_3$ | 3-F |
| A-172 | methyl | methoxy | 2-CF$_3$ | 4-F |
| A-173 | methyl | methoxy | 2-CF$_3$ | 5-F |
| A-174 | methyl | methoxy | 2-CF$_3$ | 6-F |
| A-175 | methyl | methoxy | 3-CF$_3$ | 2-F |
| A-176 | methyl | methoxy | 3-CF$_3$ | 4-F |
| A-177 | methyl | methoxy | 3-CF$_3$ | 5-F |
| A-178 | methyl | methoxy | 3-CF$_3$ | 6-F |
| A-179 | ethyl | methoxy | 2-OCHF$_2$ | — |
| A-180 | ethyl | methoxy | 3-OCHF$_2$ | — |
| A-181 | ethyl | methoxy | 4-OCHF$_2$ | — |
| A-182 | ethyl | methoxy | 2-OCF$_3$ | — |
| A-183 | ethyl | methoxy | 3-OCF$_3$ | — |
| A-184 | ethyl | methoxy | 4-OCF$_3$ | — |
| A-185 | ethyl | methoxy | 2-CF$_3$ | — |
| A-186 | ethyl | methoxy | 3-CF$_3$ | — |
| A-187 | ethyl | methoxy | 4-CF$_3$ | — |
| A-188 | ethyl | methoxy | 2-CH$_2$OCH$_3$ | — |
| A-189 | ethyl | methoxy | 3-CH$_2$OCH$_3$ | — |
| A-190 | ethyl | methoxy | 4-CH$_2$OCH$_3$ | — |
| A-191 | ethyl | methoxy | 2-CH$_2$OCH$_2$CH$_3$ | — |
| A-192 | ethyl | methoxy | 3-CH$_2$OCH$_2$CH$_3$ | — |

TABLE A-continued

| No. | R¹ | R³ | R⁵ | (R⁶)ₒ |
|---|---|---|---|---|
| A-193 | ethyl | methoxy | 4-$CH_2OCH_2CH_3$ | — |
| A-194 | ethyl | methoxy | 2-$CH_2OCF_3$ | — |
| A-195 | ethyl | methoxy | 3-$CH_2OCF_3$ | — |
| A-196 | ethyl | methoxy | 4-$CH_2OCF_3$ | — |
| A-197 | ethyl | methoxy | 2-$CH_2OCH_2CF_3$ | — |
| A-198 | ethyl | methoxy | 3-$CH_2OCH_2CF_3$ | — |
| A-199 | ethyl | methoxy | 4-$CH_2OCH_2CF_3$ | — |
| A-200 | ethyl | methoxy | 2-$CH(CH_3)OCH_3$ | — |
| A-201 | ethyl | methoxy | 3-$CH(CH_3)OCH_3$ | — |
| A-202 | ethyl | methoxy | 4-$CH(CH_3)OCH_3$ | — |
| A-203 | ethyl | methoxy | 2-$CH(CH_3)OCH_2CH_3$ | — |
| A-204 | ethyl | methoxy | 3-$CH(CH_3)OCH_2CH_3$ | — |
| A-205 | ethyl | methoxy | 4-$CH(CH_3)OCH_2CH_3$ | — |
| A-206 | ethyl | methoxy | 2-$CH(CH_3)OCF_3$ | — |
| A-207 | ethyl | methoxy | 3-$CH(CH_3)OCF_3$ | — |
| A-208 | ethyl | methoxy | 4-$CH(CH_3)OCF_3$ | — |
| A-209 | ethyl | methoxy | 2-$CH(CH_3)OCH_2CF_3$ | — |
| A-210 | ethyl | methoxy | 3-$CH(CH_3)OCH_2CF_3$ | — |
| A-211 | ethyl | methoxy | 4-$CH(CH_3)OCH_2CF_3$ | — |
| A-212 | ethyl | methoxy | 2-$OCHF_2$ | 3-methyl |
| A-213 | ethyl | methoxy | 2-$OCHF_2$ | 4-methyl |
| A-214 | ethyl | methoxy | 2-$OCHF_2$ | 5-methyl |
| A-215 | ethyl | methoxy | 2-$OCHF_2$ | 6-methyl |
| A-216 | ethyl | methoxy | 3-$OCHF_2$ | 2-methyl |
| A-217 | ethyl | methoxy | 3-$OCHF_2$ | 4-methyl |
| A-218 | ethyl | methoxy | 3-$OCHF_2$ | 5-methyl |
| A-219 | ethyl | methoxy | 3-$OCHF_2$ | 6-methyl |
| A-220 | ethyl | methoxy | 2-$OCHF_2$ | 3-F |
| A-221 | ethyl | methoxy | 2-$OCHF_2$ | 4-F |
| A-222 | ethyl | methoxy | 2-$OCHF_2$ | 5-F |
| A-223 | ethyl | methoxy | 2-$OCHF_2$ | 6-F |
| A-224 | ethyl | methoxy | 3-$OCHF_2$ | 2-F |
| A-225 | ethyl | methoxy | 3-$OCHF_2$ | 4-F |
| A-226 | ethyl | methoxy | 3-$OCHF_2$ | 5-F |
| A-227 | ethyl | methoxy | 3-$OCHF_2$ | 6-F |
| A-228 | ethyl | methoxy | 2-$OCHF_2$ | 3-Cl |
| A-229 | ethyl | methoxy | 2-$OCHF_2$ | 4-Cl |
| A-230 | ethyl | methoxy | 2-$OCHF_2$ | 5-Cl |
| A-231 | ethyl | methoxy | 2-$OCHF_2$ | 6-Cl |
| A-232 | ethyl | methoxy | 3-$OCHF_2$ | 2-Cl |
| A-233 | ethyl | methoxy | 3-$OCHF_2$ | 4-Cl |
| A-234 | ethyl | methoxy | 3-$OCHF_2$ | 5-Cl |
| A-235 | ethyl | methoxy | 3-$OCHF_2$ | 6-Cl |
| A-236 | ethyl | methoxy | 2-$CH_2OCH_3$ | 3-methyl |
| A-237 | ethyl | methoxy | 2-$CH_2OCH_3$ | 4-methyl |
| A-238 | ethyl | methoxy | 2-$CH_2OCH_3$ | 5-methyl |
| A-239 | ethyl | methoxy | 2-$CH_2OCH_3$ | 6-methyl |
| A-240 | ethyl | methoxy | 3-$CH_2OCH_3$ | 2-methyl |
| A-241 | ethyl | methoxy | 3-$CH_2OCH_3$ | 4-methyl |
| A-242 | ethyl | methoxy | 3-$CH_2OCH_3$ | 5-methyl |
| A-243 | ethyl | methoxy | 3-$CH_2OCH_3$ | 6-methyl |
| A-244 | ethyl | methoxy | 2-$CH_2OCH_3$ | 3-F |
| A-245 | ethyl | methoxy | 2-$CH_2OCH_3$ | 4-F |
| A-246 | ethyl | methoxy | 2-$CH_2OCH_3$ | 5-F |
| A-247 | ethyl | methoxy | 2-$CH_2OCH_3$ | 6-F |
| A-248 | ethyl | methoxy | 3-$CH_2OCH_3$ | 2-F |
| A-249 | ethyl | methoxy | 3-$CH_2OCH_3$ | 4-F |
| A-250 | ethyl | methoxy | 3-$CH_2OCH_3$ | 5-F |
| A-251 | ethyl | methoxy | 3-$CH_2OCH_3$ | 6-F |
| A-252 | ethyl | methoxy | 2-$CH_2OCH_3$ | 3-Cl |
| A-253 | ethyl | methoxy | 2-$CH_2OCH_3$ | 4-Cl |
| A-254 | ethyl | methoxy | 2-$CH_2OCH_3$ | 5-Cl |
| A-255 | ethyl | methoxy | 2-$CH_2OCH_3$ | 6-Cl |
| A-256 | ethyl | methoxy | 3-$CH_2OCH_3$ | 2-Cl |
| A-257 | ethyl | methoxy | 3-$CH_2OCH_3$ | 4-Cl |
| A-258 | ethyl | methoxy | 3-$CH_2OCH_3$ | 5-Cl |
| A-259 | ethyl | methoxy | 3-$CH_2OCH_3$ | 6-Cl |
| A-260 | ethyl | methoxy | 2-$CF_3$ | 3-F |
| A-261 | ethyl | methoxy | 2-$CF_3$ | 4-F |
| A-262 | ethyl | methoxy | 2-$CF_3$ | 5-F |
| A-263 | ethyl | methoxy | 2-$CF_3$ | 6-F |
| A-264 | ethyl | methoxy | 3-$CF_3$ | 2-F |
| A-265 | ethyl | methoxy | 3-$CF_3$ | 4-F |
| A-266 | ethyl | methoxy | 3-$CF_3$ | 5-F |
| A-267 | ethyl | methoxy | 3-$CF_3$ | 6-F |
| A-268 | 2-fluoroethyl | methoxy | 2-$OCHF_2$ | — |
| A-269 | 2-fluoroethyl | methoxy | 3-$OCHF_2$ | — |
| A-270 | 2-fluoroethyl | methoxy | 4-$OCHF_2$ | — |
| A-271 | 2-fluoroethyl | methoxy | 2-$OCF_3$ | — |
| A-272 | 2-fluoroethyl | methoxy | 3-$OCF_3$ | — |
| A-273 | 2-fluoroethyl | methoxy | 4-$OCF_3$ | — |
| A-274 | 2-fluoroethyl | methoxy | 2-$CF_3$ | — |
| A-275 | 2-fluoroethyl | methoxy | 3-$CF_3$ | — |
| A-276 | 2-fluoroethyl | methoxy | 4-$CF_3$ | — |
| A-277 | 2-fluoroethyl | methoxy | 2-$CH_2OCH_3$ | — |
| A-278 | 2-fluoroethyl | methoxy | 3-$CH_2OCH_3$ | — |
| A-279 | 2-fluoroethyl | methoxy | 4-$CH_2OCH_3$ | — |
| A-280 | 2-fluoroethyl | methoxy | 2-$CH_2OCH_2CH_3$ | — |
| A-281 | 2-fluoroethyl | methoxy | 3-$CH_2OCH_2CH_3$ | — |
| A-282 | 2-fluoroethyl | methoxy | 4-$CH_2OCH_2CH_3$ | — |
| A-283 | 2-fluoroethyl | methoxy | 2-$CH_2OCF_3$ | — |
| A-284 | 2-fluoroethyl | methoxy | 3-$CH_2OCF_3$ | — |
| A-285 | 2-fluoroethyl | methoxy | 4-$CH_2OCF_3$ | — |
| A-286 | 2-fluoroethyl | methoxy | 2-$CH_2OCH_2CF_3$ | — |
| A-287 | 2-fluoroethyl | methoxy | 3-$CH_2OCH_2CF_3$ | — |
| A-288 | 2-fluoroethyl | methoxy | 4-$CH_2OCH_2CF_3$ | — |
| A-289 | 2-fluoroethyl | methoxy | 2-$CH(CH_3)OCH_3$ | — |
| A-290 | 2-fluoroethyl | methoxy | 3-$CH(CH_3)OCH_3$ | — |
| A-291 | 2-fluoroethyl | methoxy | 4-$CH(CH_3)OCH_3$ | — |
| A-292 | 2-fluoroethyl | methoxy | 2-$CH(CH_3)OCH_2CH_3$ | — |
| A-293 | 2-fluoroethyl | methoxy | 3-$CH(CH_3)OCH_2CH_3$ | — |
| A-294 | 2-fluoroethyl | methoxy | 4-$CH(CH_3)OCH_2CH_3$ | — |
| A-295 | 2-fluoroethyl | methoxy | 2-$CH(CH_3)OCF_3$ | — |
| A-296 | 2-fluoroethyl | methoxy | 3-$CH(CH_3)OCF_3$ | — |
| A-297 | 2-fluoroethyl | methoxy | 4-$CH(CH_3)OCF_3$ | — |
| A-298 | 2-fluoroethyl | methoxy | 2-$CH(CH_3)OCH_2CF_3$ | — |
| A-299 | 2-fluoroethyl | methoxy | 3-$CH(CH_3)OCH_2CF_3$ | — |
| A-300 | 2-fluoroethyl | methoxy | 4-$CH(CH_3)OCH_2CF_3$ | — |
| A-301 | 2-fluoroethyl | methoxy | 2-$OCHF_2$ | 3-methyl |
| A-302 | 2-fluoroethyl | methoxy | 2-$OCHF_2$ | 4-methyl |
| A-303 | 2-fluoroethyl | methoxy | 2-$OCHF_2$ | 5-methyl |
| A-304 | 2-fluoroethyl | methoxy | 2-$OCHF_2$ | 6-methyl |
| A-305 | 2-fluoroethyl | methoxy | 3-$OCHF_2$ | 2-methyl |
| A-306 | 2-fluoroethyl | methoxy | 3-$OCHF_2$ | 4-methyl |
| A-307 | 2-fluoroethyl | methoxy | 3-$OCHF_2$ | 5-methyl |
| A-308 | 2-fluoroethyl | methoxy | 3-$OCHF_2$ | 6-methyl |
| A-309 | 2-fluoroethyl | methoxy | 2-$OCHF_2$ | 3-F |
| A-310 | 2-fluoroethyl | methoxy | 2-$OCHF_2$ | 4-F |
| A-311 | 2-fluoroethyl | methoxy | 2-$OCHF_2$ | 5-F |
| A-312 | 2-fluoroethyl | methoxy | 2-$OCHF_2$ | 6-F |
| A-313 | 2-fluoroethyl | methoxy | 3-$OCHF_2$ | 2-F |
| A-314 | 2-fluoroethyl | methoxy | 3-$OCHF_2$ | 4-F |
| A-315 | 2-fluoroethyl | methoxy | 3-$OCHF_2$ | 5-F |
| A-316 | 2-fluoroethyl | methoxy | 3-$OCHF_2$ | 6-F |
| A-317 | 2-fluoroethyl | methoxy | 2-$OCHF_2$ | 3-Cl |
| A-318 | 2-fluoroethyl | methoxy | 2-$OCHF_2$ | 4-Cl |
| A-319 | 2-fluoroethyl | methoxy | 2-$OCHF_2$ | 5-Cl |
| A-320 | 2-fluoroethyl | methoxy | 2-$OCHF_2$ | 6-Cl |
| A-321 | 2-fluoroethyl | methoxy | 3-$OCHF_2$ | 2-Cl |
| A-322 | 2-fluoroethyl | methoxy | 3-$OCHF_2$ | 4-Cl |
| A-323 | 2-fluoroethyl | methoxy | 3-$OCHF_2$ | 5-Cl |
| A-324 | 2-fluoroethyl | methoxy | 3-$OCHF_2$ | 6-Cl |
| A-325 | 2-fluoroethyl | methoxy | 2-$CH_2OCH_3$ | 3-methyl |
| A-326 | 2-fluoroethyl | methoxy | 2-$CH_2OCH_3$ | 4-methyl |
| A-327 | 2-fluoroethyl | methoxy | 2-$CH_2OCH_3$ | 5-methyl |
| A-328 | 2-fluoroethyl | methoxy | 2-$CH_2OCH_3$ | 6-methyl |
| A-329 | 2-fluoroethyl | methoxy | 3-$CH_2OCH_3$ | 2-methyl |
| A-330 | 2-fluoroethyl | methoxy | 3-$CH_2OCH_3$ | 4-methyl |
| A-331 | 2-fluoroethyl | methoxy | 3-$CH_2OCH_3$ | 5-methyl |
| A-332 | 2-fluoroethyl | methoxy | 3-$CH_2OCH_3$ | 6-methyl |
| A-333 | 2-fluoroethyl | methoxy | 2-$CH_2OCH_3$ | 3-F |
| A-334 | 2-fluoroethyl | methoxy | 2-$CH_2OCH_3$ | 4-F |
| A-335 | 2-fluoroethyl | methoxy | 2-$CH_2OCH_3$ | 5-F |
| A-336 | 2-fluoroethyl | methoxy | 2-$CH_2OCH_3$ | 6-F |
| A-337 | 2-fluoroethyl | methoxy | 3-$CH_2OCH_3$ | 2-F |
| A-338 | 2-fluoroethyl | methoxy | 3-$CH_2OCH_3$ | 4-F |
| A-339 | 2-fluoroethyl | methoxy | 3-$CH_2OCH_3$ | 5-F |
| A-340 | 2-fluoroethyl | methoxy | 3-$CH_2OCH_3$ | 6-F |
| A-341 | 2-fluoroethyl | methoxy | 2-$CH_2OCH_3$ | 3-Cl |
| A-342 | 2-fluoroethyl | methoxy | 2-$CH_2OCH_3$ | 4-Cl |
| A-343 | 2-fluoroethyl | methoxy | 2-$CH_2OCH_3$ | 5-Cl |
| A-344 | 2-fluoroethyl | methoxy | 2-$CH_2OCH_3$ | 6-Cl |
| A-345 | 2-fluoroethyl | methoxy | 3-$CH_2OCH_3$ | 2-Cl |
| A-346 | 2-fluoroethyl | methoxy | 3-$CH_2OCH_3$ | 4-Cl |
| A-347 | 2-fluoroethyl | methoxy | 3-$CH_2OCH_3$ | 5-Cl |
| A-348 | 2-fluoroethyl | methoxy | 3-$CH_2OCH_3$ | 6-Cl |

TABLE A-continued

| No. | R¹ | R³ | R⁵ | (R⁶)ₒ |
|---|---|---|---|---|
| A-349 | 2-fluoroethyl | methoxy | 2-CF₃ | 3-F |
| A-350 | 2-fluoroethyl | methoxy | 2-CF₃ | 4-F |
| A-351 | 2-fluoroethyl | methoxy | 2-CF₃ | 5-F |
| A-352 | 2-fluoroethyl | methoxy | 2-CF₃ | 6-F |
| A-353 | 2-fluoroethyl | methoxy | 3-CF₃ | 2-F |
| A-354 | 2-fluoroethyl | methoxy | 3-CF₃ | 4-F |
| A-355 | 2-fluoroethyl | methoxy | 3-CF₃ | 5-F |
| A-356 | 2-fluoroethyl | methoxy | 3-CF₃ | 6-F |
| A-357 | H | ethoxy | 2-OCHF₂ | — |
| A-358 | H | ethoxy | 3-OCHF₂ | — |
| A-359 | H | ethoxy | 4-OCHF₂ | — |
| A-360 | H | ethoxy | 2-OCF₃ | — |
| A-361 | H | ethoxy | 3-OCF₃ | — |
| A-362 | H | ethoxy | 4-OCF₃ | — |
| A-363 | H | ethoxy | 2-CF₃ | — |
| A-364 | H | ethoxy | 3-CF₃ | — |
| A-365 | H | ethoxy | 4-CF₃ | — |
| A-366 | H | ethoxy | 2-CH₂OCH₃ | — |
| A-367 | H | ethoxy | 3-CH₂OCH₃ | — |
| A-368 | H | ethoxy | 4-CH₂OCH₃ | — |
| A-369 | H | ethoxy | 2-CH₂OCH₂CH₃ | — |
| A-370 | H | ethoxy | 3-CH₂OCH₂CH₃ | — |
| A-371 | H | ethoxy | 4-CH₂OCH₂CH₃ | — |
| A-372 | H | ethoxy | 2-CH₂OCF₃ | — |
| A-373 | H | ethoxy | 3-CH₂OCF₃ | — |
| A-374 | H | ethoxy | 4-CH₂OCF₃ | — |
| A-375 | H | ethoxy | 2-CH₂OCH₂CF₃ | — |
| A-376 | H | ethoxy | 3-CH₂OCH₂CF₃ | — |
| A-377 | H | ethoxy | 4-CH₂OCH₂CF₃ | — |
| A-378 | H | ethoxy | 2-CH(CH₃)OCH₃ | — |
| A-379 | H | ethoxy | 3-CH(CH₃)OCH₃ | — |
| A-380 | H | ethoxy | 4-CH(CH₃)OCH₃ | — |
| A-381 | H | ethoxy | 2-CH(CH₃)OCH₂CH₃ | — |
| A-382 | H | ethoxy | 3-CH(CH₃)OCH₂CH₃ | — |
| A-383 | H | ethoxy | 4-CH(CH₃)OCH₂CH₃ | — |
| A-384 | H | ethoxy | 2-CH(CH₃)OCF₃ | — |
| A-385 | H | ethoxy | 3-CH(CH₃)OCF₃ | — |
| A-386 | H | ethoxy | 4-CH(CH₃)OCF₃ | — |
| A-387 | H | ethoxy | 2-CH(CH₃)OCH₂CF₃ | — |
| A-388 | H | ethoxy | 3-CH(CH₃)OCH₂CF₃ | — |
| A-389 | H | ethoxy | 4-CH(CH₃)OCH₂CF₃ | — |
| A-390 | H | ethoxy | 2-OCHF₂ | 3-methyl |
| A-391 | H | ethoxy | 2-OCHF₂ | 4-methyl |
| A-392 | H | ethoxy | 2-OCHF₂ | 5-methyl |
| A-393 | H | ethoxy | 2-OCHF₂ | 6-methyl |
| A-394 | H | ethoxy | 3-OCHF₂ | 2-methyl |
| A-395 | H | ethoxy | 3-OCHF₂ | 4-methyl |
| A-396 | H | ethoxy | 3-OCHF₂ | 5-methyl |
| A-397 | H | ethoxy | 3-OCHF₂ | 6-methyl |
| A-398 | H | ethoxy | 2-OCHF₂ | 3-F |
| A-399 | H | ethoxy | 2-OCHF₂ | 4-F |
| A-400 | H | ethoxy | 2-OCHF₂ | 5-F |
| A-401 | H | ethoxy | 2-OCHF₂ | 6-F |
| A-402 | H | ethoxy | 3-OCHF₂ | 2-F |
| A-403 | H | ethoxy | 3-OCHF₂ | 4-F |
| A-404 | H | ethoxy | 3-OCHF₂ | 5-F |
| A-405 | H | ethoxy | 3-OCHF₂ | 6-F |
| A-406 | H | ethoxy | 2-OCHF₂ | 3-Cl |
| A-407 | H | ethoxy | 2-OCHF₂ | 4-Cl |
| A-408 | H | ethoxy | 2-OCHF₂ | 5-Cl |
| A-409 | H | ethoxy | 2-OCHF₂ | 6-Cl |
| A-410 | H | ethoxy | 3-OCHF₂ | 2-Cl |
| A-411 | H | ethoxy | 3-OCHF₂ | 4-Cl |
| A-412 | H | ethoxy | 3-OCHF₂ | 5-Cl |
| A-413 | H | ethoxy | 3-OCHF₂ | 6-Cl |
| A-414 | H | ethoxy | 2-CH₂OCH₃ | 3-methyl |
| A-415 | H | ethoxy | 2-CH₂OCH₃ | 4-methyl |
| A-416 | H | ethoxy | 2-CH₂OCH₃ | 5-methyl |
| A-417 | H | ethoxy | 2-CH₂OCH₃ | 6-methyl |
| A-418 | H | ethoxy | 3-CH₂OCH₃ | 2-methyl |
| A-419 | H | ethoxy | 3-CH₂OCH₃ | 4-methyl |
| A-420 | H | ethoxy | 3-CH₂OCH₃ | 5-methyl |
| A-421 | H | ethoxy | 3-CH₂OCH₃ | 6-methyl |
| A-422 | H | ethoxy | 2-CH₂OCH₃ | 3-F |
| A-423 | H | ethoxy | 2-CH₂OCH₃ | 4-F |
| A-424 | H | ethoxy | 2-CH₂OCH₃ | 5-F |
| A-425 | H | ethoxy | 2-CH₂OCH₃ | 6-F |
| A-426 | H | ethoxy | 3-CH₂OCH₃ | 2-F |
| A-427 | H | ethoxy | 3-CH₂OCH₃ | 4-F |
| A-428 | H | ethoxy | 3-CH₂OCH₃ | 5-F |
| A-429 | H | ethoxy | 3-CH₂OCH₃ | 6-F |
| A-430 | H | ethoxy | 2-CH₂OCH₃ | 3-Cl |
| A-431 | H | ethoxy | 2-CH₂OCH₃ | 4-Cl |
| A-432 | H | ethoxy | 2-CH₂OCH₃ | 5-Cl |
| A-433 | H | ethoxy | 2-CH₂OCH₃ | 6-Cl |
| A-434 | H | ethoxy | 3-CH₂OCH₃ | 2-Cl |
| A-435 | H | ethoxy | 3-CH₂OCH₃ | 4-Cl |
| A-436 | H | ethoxy | 3-CH₂OCH₃ | 5-Cl |
| A-437 | H | ethoxy | 3-CH₂OCH₃ | 6-Cl |
| A-438 | H | ethoxy | 2-CF₃ | 3-F |
| A-439 | H | ethoxy | 2-CF₃ | 4-F |
| A-440 | H | ethoxy | 2-CF₃ | 5-F |
| A-441 | H | ethoxy | 2-CF₃ | 6-F |
| A-442 | H | ethoxy | 3-CF₃ | 2-F |
| A-443 | H | ethoxy | 3-CF₃ | 4-F |
| A-444 | H | ethoxy | 3-CF₃ | 5-F |
| A-445 | H | ethoxy | 3-CF₃ | 6-F |
| A-446 | methyl | ethoxy | 2-OCHF₂ | — |
| A-447 | methyl | ethoxy | 3-OCHF₂ | — |
| A-448 | methyl | ethoxy | 4-OCHF₂ | — |
| A-449 | methyl | ethoxy | 2-OCF₃ | — |
| A-450 | methyl | ethoxy | 3-OCF₃ | — |
| A-451 | methyl | ethoxy | 4-OCF₃ | — |
| A-452 | methyl | ethoxy | 2-CF₃ | — |
| A-453 | methyl | ethoxy | 3-CF₃ | — |
| A-454 | methyl | ethoxy | 4-CF₃ | — |
| A-455 | methyl | ethoxy | 2-CH₂OCH₃ | — |
| A-456 | methyl | ethoxy | 3-CH₂OCH₃ | — |
| A-457 | methyl | ethoxy | 4-CH₂OCH₃ | — |
| A-458 | methyl | ethoxy | 2-CH₂OCH₂CH₃ | — |
| A-459 | methyl | ethoxy | 3-CH₂OCH₂CH₃ | — |
| A-460 | methyl | ethoxy | 4-CH₂OCH₂CH₃ | — |
| A-461 | methyl | ethoxy | 2-CH₂OCF₃ | — |
| A-462 | methyl | ethoxy | 3-CH₂OCF₃ | — |
| A-463 | methyl | ethoxy | 4-CH₂OCF₃ | — |
| A-464 | methyl | ethoxy | 2-CH₂OCH₂CF₃ | — |
| A-465 | methyl | ethoxy | 3-CH₂OCH₂CF₃ | — |
| A-466 | methyl | ethoxy | 4-CH₂OCH₂CF₃ | — |
| A-467 | methyl | ethoxy | 2-CH(CH₃)OCH₃ | — |
| A-468 | methyl | ethoxy | 3-CH(CH₃)OCH₃ | — |
| A-469 | methyl | ethoxy | 4-CH(CH₃)OCH₃ | — |
| A-470 | methyl | ethoxy | 2-CH(CH₃)OCH₂CH₃ | — |
| A-471 | methyl | ethoxy | 3-CH(CH₃)OCH₂CH₃ | — |
| A-472 | methyl | ethoxy | 4-CH(CH₃)OCH₂CH₃ | — |
| A-473 | methyl | ethoxy | 2-CH(CH₃)OCF₃ | — |
| A-474 | methyl | ethoxy | 3-CH(CH₃)OCF₃ | — |
| A-475 | methyl | ethoxy | 4-CH(CH₃)OCF₃ | — |
| A-476 | methyl | ethoxy | 2-CH(CH₃)OCH₂CF₃ | — |
| A-477 | methyl | ethoxy | 3-CH(CH₃)OCH₂CF₃ | — |
| A-478 | methyl | ethoxy | 4-CH(CH₃)OCH₂CF₃ | — |
| A-479 | methyl | ethoxy | 2-OCHF₂ | 3-methyl |
| A-480 | methyl | ethoxy | 2-OCHF₂ | 4-methyl |
| A-481 | methyl | ethoxy | 2-OCHF₂ | 5-methyl |
| A-482 | methyl | ethoxy | 2-OCHF₂ | 6-methyl |
| A-483 | methyl | ethoxy | 3-OCHF₂ | 2-methyl |
| A-484 | methyl | ethoxy | 3-OCHF₂ | 4-methyl |
| A-485 | methyl | ethoxy | 3-OCHF₂ | 5-methyl |
| A-486 | methyl | ethoxy | 3-OCHF₂ | 6-methyl |
| A-487 | methyl | ethoxy | 2-OCHF₂ | 3-F |
| A-488 | methyl | ethoxy | 2-OCHF₂ | 4-F |
| A-489 | methyl | ethoxy | 2-OCHF₂ | 5-F |
| A-490 | methyl | ethoxy | 2-OCHF₂ | 6-F |
| A-491 | methyl | ethoxy | 3-OCHF₂ | 2-F |
| A-492 | methyl | ethoxy | 3-OCHF₂ | 4-F |
| A-493 | methyl | ethoxy | 3-OCHF₂ | 5-F |
| A-494 | methyl | ethoxy | 3-OCHF₂ | 6-F |
| A-495 | methyl | ethoxy | 2-OCHF₂ | 3-Cl |
| A-496 | methyl | ethoxy | 2-OCHF₂ | 4-Cl |
| A-497 | methyl | ethoxy | 2-OCHF₂ | 5-Cl |
| A-498 | methyl | ethoxy | 2-OCHF₂ | 6-Cl |
| A-499 | methyl | ethoxy | 3-OCHF₂ | 2-Cl |
| A-500 | methyl | ethoxy | 3-OCHF₂ | 4-Cl |
| A-501 | methyl | ethoxy | 3-OCHF₂ | 5-Cl |
| A-502 | methyl | ethoxy | 3-OCHF₂ | 6-Cl |
| A-503 | methyl | ethoxy | 2-CH₂OCH₃ | 3-methyl |
| A-504 | methyl | ethoxy | 2-CH₂OCH₃ | 4-methyl |

TABLE A-continued

| No. | R¹ | R³ | R⁵ | (R⁶)ₒ |
|---|---|---|---|---|
| A-505 | methyl | ethoxy | 2-CH$_2$OCH$_3$ | 5-methyl |
| A-506 | methyl | ethoxy | 2-CH$_2$OCH$_3$ | 6-methyl |
| A-507 | methyl | ethoxy | 3-CH$_2$OCH$_3$ | 2-methyl |
| A-508 | methyl | ethoxy | 3-CH$_2$OCH$_3$ | 4-methyl |
| A-509 | methyl | ethoxy | 3-CH$_2$OCH$_3$ | 5-methyl |
| A-510 | methyl | ethoxy | 3-CH$_2$OCH$_3$ | 6-methyl |
| A-511 | methyl | ethoxy | 2-CH$_2$OCH$_3$ | 3-F |
| A-512 | methyl | ethoxy | 2-CH$_2$OCH$_3$ | 4-F |
| A-513 | methyl | ethoxy | 2-CH$_2$OCH$_3$ | 5-F |
| A-514 | methyl | ethoxy | 2-CH$_2$OCH$_3$ | 6-F |
| A-515 | methyl | ethoxy | 3-CH$_2$OCH$_3$ | 2-F |
| A-516 | methyl | ethoxy | 3-CH$_2$OCH$_3$ | 4-F |
| A-517 | methyl | ethoxy | 3-CH$_2$OCH$_3$ | 5-F |
| A-518 | methyl | ethoxy | 3-CH$_2$OCH$_3$ | 6-F |
| A-519 | methyl | ethoxy | 2-CH$_2$OCH$_3$ | 3-Cl |
| A-520 | methyl | ethoxy | 2-CH$_2$OCH$_3$ | 4-Cl |
| A-521 | methyl | ethoxy | 2-CH$_2$OCH$_3$ | 5-Cl |
| A-522 | methyl | ethoxy | 2-CH$_2$OCH$_3$ | 6-Cl |
| A-523 | methyl | ethoxy | 3-CH$_2$OCH$_3$ | 2-Cl |
| A-524 | methyl | ethoxy | 3-CH$_2$OCH$_3$ | 4-Cl |
| A-525 | methyl | ethoxy | 3-CH$_2$OCH$_3$ | 5-Cl |
| A-526 | methyl | ethoxy | 3-CH$_2$OCH$_3$ | 6-Cl |
| A-527 | methyl | ethoxy | 2-CF$_3$ | 3-F |
| A-528 | methyl | ethoxy | 2-CF$_3$ | 4-F |
| A-529 | methyl | ethoxy | 2-CF$_3$ | 5-F |
| A-530 | methyl | ethoxy | 2-CF$_3$ | 6-F |
| A-531 | methyl | ethoxy | 3-CF$_3$ | 2-F |
| A-532 | methyl | ethoxy | 3-CF$_3$ | 4-F |
| A-533 | methyl | ethoxy | 3-CF$_3$ | 5-F |
| A-534 | methyl | ethoxy | 3-CF$_3$ | 6-F |
| A-535 | ethyl | ethoxy | 2-OCHF$_2$ | — |
| A-536 | ethyl | ethoxy | 3-OCHF$_2$ | — |
| A-537 | ethyl | ethoxy | 4-OCHF$_2$ | — |
| A-538 | ethyl | ethoxy | 2-OCF$_3$ | — |
| A-539 | ethyl | ethoxy | 3-OCF$_3$ | — |
| A-540 | ethyl | ethoxy | 4-OCF$_3$ | — |
| A-541 | ethyl | ethoxy | 2-CF$_3$ | — |
| A-542 | ethyl | ethoxy | 3-CF$_3$ | — |
| A-543 | ethyl | ethoxy | 4-CF$_3$ | — |
| A-544 | ethyl | ethoxy | 2-CH$_2$OCH$_3$ | — |
| A-545 | ethyl | ethoxy | 3-CH$_2$OCH$_3$ | — |
| A-546 | ethyl | ethoxy | 4-CH$_2$OCH$_3$ | — |
| A-547 | ethyl | ethoxy | 2-CH$_2$OCH$_2$CH$_3$ | — |
| A-548 | ethyl | ethoxy | 3-CH$_2$OCH$_2$CH$_3$ | — |
| A-549 | ethyl | ethoxy | 4-CH$_2$OCH$_2$CH$_3$ | — |
| A-550 | ethyl | ethoxy | 2-CH$_2$OCF$_3$ | — |
| A-551 | ethyl | ethoxy | 3-CH$_2$OCF$_3$ | — |
| A-552 | ethyl | ethoxy | 4-CH$_2$OCF$_3$ | — |
| A-553 | ethyl | ethoxy | 2-CH$_2$OCH$_2$CF$_3$ | — |
| A-554 | ethyl | ethoxy | 3-CH$_2$OCH$_2$CF$_3$ | — |
| A-555 | ethyl | ethoxy | 4-CH$_2$OCH$_2$CF$_3$ | — |
| A-556 | ethyl | ethoxy | 2-CH(CH$_3$)OCH$_3$ | — |
| A-557 | ethyl | ethoxy | 3-CH(CH$_3$)OCH$_3$ | — |
| A-558 | ethyl | ethoxy | 4-CH(CH$_3$)OCH$_3$ | — |
| A-559 | ethyl | ethoxy | 2-CH(CH$_3$)OCH$_2$CH$_3$ | — |
| A-560 | ethyl | ethoxy | 3-CH(CH$_3$)OCH$_2$CH$_3$ | — |
| A-561 | ethyl | ethoxy | 4-CH(CH$_3$)OCH$_2$CH$_3$ | — |
| A-562 | ethyl | ethoxy | 2-CH(CH$_3$)OCF$_3$ | — |
| A-563 | ethyl | ethoxy | 3-CH(CH$_3$)OCF$_3$ | — |
| A-564 | ethyl | ethoxy | 4-CH(CH$_3$)OCF$_3$ | — |
| A-565 | ethyl | ethoxy | 2-CH(CH$_3$)OCH$_2$CF$_3$ | — |
| A-566 | ethyl | ethoxy | 3-CH(CH$_3$)OCH$_2$CF$_3$ | — |
| A-567 | ethyl | ethoxy | 4-CH(CH$_3$)OCH$_2$CF$_3$ | — |
| A-568 | ethyl | ethoxy | 2-OCHF$_2$ | 3-methyl |
| A-569 | ethyl | ethoxy | 2-OCHF$_2$ | 4-methyl |
| A-570 | ethyl | ethoxy | 2-OCHF$_2$ | 5-methyl |
| A-571 | ethyl | ethoxy | 2-OCHF$_2$ | 6-methyl |
| A-572 | ethyl | ethoxy | 3-OCHF$_2$ | 2-methyl |
| A-573 | ethyl | ethoxy | 3-OCHF$_2$ | 4-methyl |
| A-574 | ethyl | ethoxy | 3-OCHF$_2$ | 5-methyl |
| A-575 | ethyl | ethoxy | 3-OCHF$_2$ | 6-methyl |
| A-576 | ethyl | ethoxy | 2-OCHF$_2$ | 3-F |
| A-577 | ethyl | ethoxy | 2-OCHF$_2$ | 4-F |
| A-578 | ethyl | ethoxy | 2-OCHF$_2$ | 5-F |
| A-579 | ethyl | ethoxy | 2-OCHF$_2$ | 6-F |
| A-580 | ethyl | ethoxy | 3-OCHF$_2$ | 2-F |
| A-581 | ethyl | ethoxy | 3-OCHF$_2$ | 4-F |
| A-582 | ethyl | ethoxy | 3-OCHF$_2$ | 5-F |
| A-583 | ethyl | ethoxy | 3-OCHF$_2$ | 6-F |
| A-584 | ethyl | ethoxy | 2-OCHF$_2$ | 3-Cl |
| A-585 | ethyl | ethoxy | 2-OCHF$_2$ | 4-Cl |
| A-586 | ethyl | ethoxy | 2-OCHF$_2$ | 5-Cl |
| A-587 | ethyl | ethoxy | 2-OCHF$_2$ | 6-Cl |
| A-588 | ethyl | ethoxy | 3-OCHF$_2$ | 2-Cl |
| A-589 | ethyl | ethoxy | 3-OCHF$_2$ | 4-Cl |
| A-590 | ethyl | ethoxy | 3-OCHF$_2$ | 5-Cl |
| A-591 | ethyl | ethoxy | 3-OCHF$_2$ | 6-Cl |
| A-592 | ethyl | ethoxy | 2-CH$_2$OCH$_3$ | 3-methyl |
| A-593 | ethyl | ethoxy | 2-CH$_2$OCH$_3$ | 4-methyl |
| A-594 | ethyl | ethoxy | 2-CH$_2$OCH$_3$ | 5-methyl |
| A-595 | ethyl | ethoxy | 2-CH$_2$OCH$_3$ | 6-methyl |
| A-596 | ethyl | ethoxy | 3-CH$_2$OCH$_3$ | 2-methyl |
| A-597 | ethyl | ethoxy | 3-CH$_2$OCH$_3$ | 4-methyl |
| A-598 | ethyl | ethoxy | 3-CH$_2$OCH$_3$ | 5-methyl |
| A-599 | ethyl | ethoxy | 3-CH$_2$OCH$_3$ | 6-methyl |
| A-600 | ethyl | ethoxy | 2-CH$_2$OCH$_3$ | 3-F |
| A-601 | ethyl | ethoxy | 2-CH$_2$OCH$_3$ | 4-F |
| A-602 | ethyl | ethoxy | 2-CH$_2$OCH$_3$ | 5-F |
| A-603 | ethyl | ethoxy | 2-CH$_2$OCH$_3$ | 6-F |
| A-604 | ethyl | ethoxy | 3-CH$_2$OCH$_3$ | 2-F |
| A-605 | ethyl | ethoxy | 3-CH$_2$OCH$_3$ | 4-F |
| A-606 | ethyl | ethoxy | 3-CH$_2$OCH$_3$ | 5-F |
| A-607 | ethyl | ethoxy | 3-CH$_2$OCH$_3$ | 6-F |
| A-608 | ethyl | ethoxy | 2-CH$_2$OCH$_3$ | 3-Cl |
| A-609 | ethyl | ethoxy | 2-CH$_2$OCH$_3$ | 4-Cl |
| A-610 | ethyl | ethoxy | 2-CH$_2$OCH$_3$ | 5-Cl |
| A-611 | ethyl | ethoxy | 2-CH$_2$OCH$_3$ | 6-Cl |
| A-612 | ethyl | ethoxy | 3-CH$_2$OCH$_3$ | 2-Cl |
| A-613 | ethyl | ethoxy | 3-CH$_2$OCH$_3$ | 4-Cl |
| A-614 | ethyl | ethoxy | 3-CH$_2$OCH$_3$ | 5-Cl |
| A-615 | ethyl | ethoxy | 3-CH$_2$OCH$_3$ | 6-Cl |
| A-616 | ethyl | ethoxy | 2-CF$_3$ | 3-F |
| A-617 | ethyl | ethoxy | 2-CF$_3$ | 4-F |
| A-618 | ethyl | ethoxy | 2-CF$_3$ | 5-F |
| A-619 | ethyl | ethoxy | 2-CF$_3$ | 6-F |
| A-620 | ethyl | ethoxy | 3-CF$_3$ | 2-F |
| A-621 | ethyl | ethoxy | 3-CF$_3$ | 4-F |
| A-622 | ethyl | ethoxy | 3-CF$_3$ | 5-F |
| A-623 | ethyl | ethoxy | 3-CF$_3$ | 6-F |
| A-624 | 2-fluoroethyl | ethoxy | 2-OCHF$_2$ | — |
| A-625 | 2-fluoroethyl | ethoxy | 3-OCHF$_2$ | — |
| A-626 | 2-fluoroethyl | ethoxy | 4-OCHF$_2$ | — |
| A-627 | 2-fluoroethyl | ethoxy | 2-OCF$_3$ | — |
| A-628 | 2-fluoroethyl | ethoxy | 3-OCF$_3$ | — |
| A-629 | 2-fluoroethyl | ethoxy | 4-OCF$_3$ | — |
| A-630 | 2-fluoroethyl | ethoxy | 2-CF$_3$ | — |
| A-631 | 2-fluoroethyl | ethoxy | 3-CF$_3$ | — |
| A-632 | 2-fluoroethyl | ethoxy | 4-CF$_3$ | — |
| A-633 | 2-fluoroethyl | ethoxy | 2-CH$_2$OCH$_3$ | — |
| A-634 | 2-fluoroethyl | ethoxy | 3-CH$_2$OCH$_3$ | — |
| A-635 | 2-fluoroethyl | ethoxy | 4-CH$_2$OCH$_3$ | — |
| A-636 | 2-fluoroethyl | ethoxy | 2-CH$_2$OCH$_2$CH$_3$ | — |
| A-637 | 2-fluoroethyl | ethoxy | 3-CH$_2$OCH$_2$CH$_3$ | — |
| A-638 | 2-fluoroethyl | ethoxy | 4-CH$_2$OCH$_2$CH$_3$ | — |
| A-639 | 2-fluoroethyl | ethoxy | 2-CH$_2$OCF$_3$ | — |
| A-640 | 2-fluoroethyl | ethoxy | 3-CH$_2$OCF$_3$ | — |
| A-641 | 2-fluoroethyl | ethoxy | 4-CH$_2$OCF$_3$ | — |
| A-642 | 2-fluoroethyl | ethoxy | 2-CH$_2$OCH$_2$CF$_3$ | — |
| A-643 | 2-fluoroethyl | ethoxy | 3-CH$_2$OCH$_2$CF$_3$ | — |
| A-644 | 2-fluoroethyl | ethoxy | 4-CH$_2$OCH$_2$CF$_3$ | — |
| A-645 | 2-fluoroethyl | ethoxy | 2-CH(CH$_3$)OCH$_3$ | — |
| A-646 | 2-fluoroethyl | ethoxy | 3-CH(CH$_3$)OCH$_3$ | — |
| A-647 | 2-fluoroethyl | ethoxy | 4-CH(CH$_3$)OCH$_3$ | — |
| A-648 | 2-fluoroethyl | ethoxy | 2-CH(CH$_3$)OCH$_2$CH$_3$ | — |
| A-649 | 2-fluoroethyl | ethoxy | 3-CH(CH$_3$)OCH$_2$CH$_3$ | — |
| A-650 | 2-fluoroethyl | ethoxy | 4-CH(CH$_3$)OCH$_2$CH$_3$ | — |
| A-651 | 2-fluoroethyl | ethoxy | 2-CH(CH$_3$)OCF$_3$ | — |
| A-652 | 2-fluoroethyl | ethoxy | 3-CH(CH$_3$)OCF$_3$ | — |
| A-653 | 2-fluoroethyl | ethoxy | 4-CH(CH$_3$)OCF$_3$ | — |
| A-654 | 2-fluoroethyl | ethoxy | 2-CH(CH$_3$)OCH$_2$CF$_3$ | — |
| A-655 | 2-fluoroethyl | ethoxy | 3-CH(CH$_3$)OCH$_2$CF$_3$ | — |
| A-656 | 2-fluoroethyl | ethoxy | 4-CH(CH$_3$)OCH$_2$CF$_3$ | — |
| A-657 | 2-fluoroethyl | ethoxy | 2-OCHF$_2$ | 3-methyl |
| A-658 | 2-fluoroethyl | ethoxy | 2-OCHF$_2$ | 4-methyl |
| A-659 | 2-fluoroethyl | ethoxy | 2-OCHF$_2$ | 5-methyl |
| A-660 | 2-fluoroethyl | ethoxy | 2-OCHF$_2$ | 6-methyl |

TABLE A-continued

| No. | R¹ | R³ | R⁵ | (R⁶)ₒ |
|---|---|---|---|---|
| A-661 | 2-fluoroethyl | ethoxy | 3-OCHF$_2$ | 2-methyl |
| A-662 | 2-fluoroethyl | ethoxy | 3-OCHF$_2$ | 4-methyl |
| A-663 | 2-fluoroethyl | ethoxy | 3-OCHF$_2$ | 5-methyl |
| A-664 | 2-fluoroethyl | ethoxy | 3-OCHF$_2$ | 6-methyl |
| A-665 | 2-fluoroethyl | ethoxy | 2-OCHF$_2$ | 3-F |
| A-666 | 2-fluoroethyl | ethoxy | 2-OCHF$_2$ | 4-F |
| A-667 | 2-fluoroethyl | ethoxy | 2-OCHF$_2$ | 5-F |
| A-668 | 2-fluoroethyl | ethoxy | 2-OCHF$_2$ | 6-F |
| A-669 | 2-fluoroethyl | ethoxy | 3-OCHF$_2$ | 2-F |
| A-670 | 2-fluoroethyl | ethoxy | 3-OCHF$_2$ | 4-F |
| A-671 | 2-fluoroethyl | ethoxy | 3-OCHF$_2$ | 5-F |
| A-672 | 2-fluoroethyl | ethoxy | 3-OCHF$_2$ | 6-F |
| A-673 | 2-fluoroethyl | ethoxy | 2-OCHF$_2$ | 3-Cl |
| A-674 | 2-fluoroethyl | ethoxy | 2-OCHF$_2$ | 4-Cl |
| A-675 | 2-fluoroethyl | ethoxy | 2-OCHF$_2$ | 5-Cl |
| A-676 | 2-fluoroethyl | ethoxy | 2-OCHF$_2$ | 6-Cl |
| A-677 | 2-fluoroethyl | ethoxy | 3-OCHF$_2$ | 2-Cl |
| A-678 | 2-fluoroethyl | ethoxy | 3-OCHF$_2$ | 4-Cl |
| A-679 | 2-fluoroethyl | ethoxy | 3-OCHF$_2$ | 5-Cl |
| A-680 | 2-fluoroethyl | ethoxy | 3-OCHF$_2$ | 6-Cl |
| A-681 | 2-fluoroethyl | ethoxy | 2-CH$_2$OCH$_3$ | 3-methyl |
| A-682 | 2-fluoroethyl | ethoxy | 2-CH$_2$OCH$_3$ | 4-methyl |
| A-683 | 2-fluoroethyl | ethoxy | 2-CH$_2$OCH$_3$ | 5-methyl |
| A-684 | 2-fluoroethyl | ethoxy | 2-CH$_2$OCH$_3$ | 6-methyl |
| A-685 | 2-fluoroethyl | ethoxy | 3-CH$_2$OCH$_3$ | 2-methyl |
| A-686 | 2-fluoroethyl | ethoxy | 3-CH$_2$OCH$_3$ | 4-methyl |
| A-687 | 2-fluoroethyl | ethoxy | 3-CH$_2$OCH$_3$ | 5-methyl |
| A-688 | 2-fluoroethyl | ethoxy | 3-CH$_2$OCH$_3$ | 6-methyl |
| A-689 | 2-fluoroethyl | ethoxy | 2-CH$_2$OCH$_3$ | 3-F |
| A-690 | 2-fluoroethyl | ethoxy | 2-CH$_2$OCH$_3$ | 4-F |
| A-691 | 2-fluoroethyl | ethoxy | 2-CH$_2$OCH$_3$ | 5-F |
| A-692 | 2-fluoroethyl | ethoxy | 2-CH$_2$OCH$_3$ | 6-F |
| A-693 | 2-fluoroethyl | ethoxy | 3-CH$_2$OCH$_3$ | 2-F |
| A-694 | 2-fluoroethyl | ethoxy | 3-CH$_2$OCH$_3$ | 4-F |
| A-695 | 2-fluoroethyl | ethoxy | 3-CH$_2$OCH$_3$ | 5-F |
| A-696 | 2-fluoroethyl | ethoxy | 3-CH$_2$OCH$_3$ | 6-F |
| A-697 | 2-fluoroethyl | ethoxy | 2-CH$_2$OCH$_3$ | 3-Cl |
| A-698 | 2-fluoroethyl | ethoxy | 2-CH$_2$OCH$_3$ | 4-Cl |
| A-699 | 2-fluoroethyl | ethoxy | 2-CH$_2$OCH$_3$ | 5-Cl |
| A-700 | 2-fluoroethyl | ethoxy | 2-CH$_2$OCH$_3$ | 6-Cl |
| A-701 | 2-fluoroethyl | ethoxy | 3-CH$_2$OCH$_3$ | 2-Cl |
| A-702 | 2-fluoroethyl | ethoxy | 3-CH$_2$OCH$_3$ | 4-Cl |
| A-703 | 2-fluoroethyl | ethoxy | 3-CH$_2$OCH$_3$ | 5-Cl |
| A-704 | 2-fluoroethyl | ethoxy | 3-CH$_2$OCH$_3$ | 6-Cl |
| A-705 | 2-fluoroethyl | ethoxy | 2-CF$_3$ | 3-F |
| A-706 | 2-fluoroethyl | ethoxy | 2-CF$_3$ | 4-F |
| A-707 | 2-fluoroethyl | ethoxy | 2-CF$_3$ | 5-F |
| A-708 | 2-fluoroethyl | ethoxy | 2-CF$_3$ | 6-F |
| A-709 | 2-fluoroethyl | ethoxy | 3-CF$_3$ | 2-F |
| A-710 | 2-fluoroethyl | ethoxy | 3-CF$_3$ | 4-F |
| A-711 | 2-fluoroethyl | ethoxy | 3-CF$_3$ | 5-F |
| A-712 | 2-fluoroethyl | ethoxy | 3-CF$_3$ | 6-F |
| A-713 | H | methyl | 2-OCHF$_2$ | — |
| A-714 | H | methyl | 3-OCHF$_2$ | — |
| A-715 | H | methyl | 4-OCHF$_2$ | — |
| A-716 | H | methyl | 2-OCF$_3$ | — |
| A-717 | H | methyl | 3-OCF$_3$ | — |
| A-718 | H | methyl | 4-OCF$_3$ | — |
| A-719 | H | methyl | 2-CF$_3$ | — |
| A-720 | H | methyl | 3-CF$_3$ | — |
| A-721 | H | methyl | 4-CF$_3$ | — |
| A-722 | H | methyl | 2-CH$_2$OCH$_3$ | — |
| A-723 | H | methyl | 3-CH$_2$OCH$_3$ | — |
| A-724 | H | methyl | 4-CH$_2$OCH$_3$ | — |
| A-725 | H | methyl | 2-CH$_2$OCH$_2$CH$_3$ | — |
| A-726 | H | methyl | 3-CH$_2$OCH$_2$CH$_3$ | — |
| A-727 | H | methyl | 4-CH$_2$OCH$_2$CH$_3$ | — |
| A-728 | H | methyl | 2-CH$_2$OCF$_3$ | — |
| A-729 | H | methyl | 3-CH$_2$OCF$_3$ | — |
| A-730 | H | methyl | 4-CH$_2$OCF$_3$ | — |
| A-731 | H | methyl | 2-CH$_2$OCH$_2$CF$_3$ | — |
| A-732 | H | methyl | 3-CH$_2$OCH$_2$CF$_3$ | — |
| A-733 | H | methyl | 4-CH$_2$OCH$_2$CF$_3$ | — |
| A-734 | H | methyl | 2-CH(CH$_3$)OCH$_3$ | — |
| A-735 | H | methyl | 3-CH(CH$_3$)OCH$_3$ | — |
| A-736 | H | methyl | 4-CH(CH$_3$)OCH$_3$ | — |
| A-737 | H | methyl | 2-CH(CH$_3$)OCH$_2$CH$_3$ | — |
| A-738 | H | methyl | 3-CH(CH$_3$)OCH$_2$CH$_3$ | — |
| A-739 | H | methyl | 4-CH(CH$_3$)OCH$_2$CH$_3$ | — |
| A-740 | H | methyl | 2-CH(CH$_3$)OCF$_3$ | — |
| A-741 | H | methyl | 3-CH(CH$_3$)OCF$_3$ | — |
| A-742 | H | methyl | 4-CH(CH$_3$)OCF$_3$ | — |
| A-743 | H | methyl | 2-CH(CH$_3$)OCH$_2$CF$_3$ | — |
| A-744 | H | methyl | 3-CH(CH$_3$)OCH$_2$CF$_3$ | — |
| A-745 | H | methyl | 4-CH(CH$_3$)OCH$_2$CF$_3$ | — |
| A-746 | H | methyl | 2-OCHF$_2$ | 3-methyl |
| A-747 | H | methyl | 2-OCHF$_2$ | 4-methyl |
| A-748 | H | methyl | 2-OCHF$_2$ | 5-methyl |
| A-749 | H | methyl | 2-OCHF$_2$ | 6-methyl |
| A-750 | H | methyl | 3-OCHF$_2$ | 2-methyl |
| A-751 | H | methyl | 3-OCHF$_2$ | 4-methyl |
| A-752 | H | methyl | 3-OCHF$_2$ | 5-methyl |
| A-753 | H | methyl | 3-OCHF$_2$ | 6-methyl |
| A-754 | H | methyl | 2-OCHF$_2$ | 3-F |
| A-755 | H | methyl | 2-OCHF$_2$ | 4-F |
| A-756 | H | methyl | 2-OCHF$_2$ | 5-F |
| A-757 | H | methyl | 2-OCHF$_2$ | 6-F |
| A-758 | H | methyl | 3-OCHF$_2$ | 2-F |
| A-759 | H | methyl | 3-OCHF$_2$ | 4-F |
| A-760 | H | methyl | 3-OCHF$_2$ | 5-F |
| A-761 | H | methyl | 3-OCHF$_2$ | 6-F |
| A-762 | H | methyl | 2-OCHF$_2$ | 3-Cl |
| A-763 | H | methyl | 2-OCHF$_2$ | 4-Cl |
| A-764 | H | methyl | 2-OCHF$_2$ | 5-Cl |
| A-765 | H | methyl | 2-OCHF$_2$ | 6-Cl |
| A-766 | H | methyl | 3-OCHF$_2$ | 2-Cl |
| A-767 | H | methyl | 3-OCHF$_2$ | 4-Cl |
| A-768 | H | methyl | 3-OCHF$_2$ | 5-Cl |
| A-769 | H | methyl | 3-OCHF$_2$ | 6-Cl |
| A-770 | H | methyl | 2-CH$_2$OCH$_3$ | 3-methyl |
| A-771 | H | methyl | 2-CH$_2$OCH$_3$ | 4-methyl |
| A-772 | H | methyl | 2-CH$_2$OCH$_3$ | 5-methyl |
| A-773 | H | methyl | 2-CH$_2$OCH$_3$ | 6-methyl |
| A-774 | H | methyl | 3-CH$_2$OCH$_3$ | 2-methyl |
| A-775 | H | methyl | 3-CH$_2$OCH$_3$ | 4-methyl |
| A-776 | H | methyl | 3-CH$_2$OCH$_3$ | 5-methyl |
| A-777 | H | methyl | 3-CH$_2$OCH$_3$ | 6-methyl |
| A-778 | H | methyl | 2-CH$_2$OCH$_3$ | 3-F |
| A-779 | H | methyl | 2-CH$_2$OCH$_3$ | 4-F |
| A-780 | H | methyl | 2-CH$_2$OCH$_3$ | 5-F |
| A-781 | H | methyl | 2-CH$_2$OCH$_3$ | 6-F |
| A-782 | H | methyl | 3-CH$_2$OCH$_3$ | 2-F |
| A-783 | H | methyl | 3-CH$_2$OCH$_3$ | 4-F |
| A-784 | H | methyl | 3-CH$_2$OCH$_3$ | 5-F |
| A-785 | H | methyl | 3-CH$_2$OCH$_3$ | 6-F |
| A-786 | H | methyl | 2-CH$_2$OCH$_3$ | 3-Cl |
| A-787 | H | methyl | 2-CH$_2$OCH$_3$ | 4-Cl |
| A-788 | H | methyl | 2-CH$_2$OCH$_3$ | 5-Cl |
| A-789 | H | methyl | 2-CH$_2$OCH$_3$ | 6-Cl |
| A-790 | H | methyl | 3-CH$_2$OCH$_3$ | 2-Cl |
| A-791 | H | methyl | 3-CH$_2$OCH$_3$ | 4-Cl |
| A-792 | H | methyl | 3-CH$_2$OCH$_3$ | 5-Cl |
| A-793 | H | methyl | 3-CH$_2$OCH$_3$ | 6-Cl |
| A-794 | H | methyl | 2-CF$_3$ | 3-F |
| A-795 | H | methyl | 2-CF$_3$ | 4-F |
| A-796 | H | methyl | 2-CF$_3$ | 5-F |
| A-797 | H | methyl | 2-CF$_3$ | 6-F |
| A-798 | H | methyl | 3-CF$_3$ | 2-F |
| A-799 | H | methyl | 3-CF$_3$ | 4-F |
| A-800 | H | methyl | 3-CF$_3$ | 5-F |
| A-801 | H | methyl | 3-CF$_3$ | 6-F |
| A-802 | methyl | methyl | 2-OCHF$_2$ | — |
| A-803 | methyl | methyl | 3-OCHF$_2$ | — |
| A-804 | methyl | methyl | 4-OCHF$_2$ | — |
| A-805 | methyl | methyl | 2-OCF$_3$ | — |
| A-806 | methyl | methyl | 3-OCF$_3$ | — |
| A-807 | methyl | methyl | 4-OCF$_3$ | — |
| A-808 | methyl | methyl | 2-CF$_3$ | — |
| A-809 | methyl | methyl | 3-CF$_3$ | — |
| A-810 | methyl | methyl | 4-CF$_3$ | — |
| A-811 | methyl | methyl | 2-CH$_2$OCH$_3$ | — |
| A-812 | methyl | methyl | 3-CH$_2$OCH$_3$ | — |
| A-813 | methyl | methyl | 4-CH$_2$OCH$_3$ | — |
| A-814 | methyl | methyl | 2-CH$_2$OCH$_2$CH$_3$ | — |
| A-815 | methyl | methyl | 3-CH$_2$OCH$_2$CH$_3$ | — |
| A-816 | methyl | methyl | 4-CH$_2$OCH$_2$CH$_3$ | — |

TABLE A-continued

| No. | R¹ | R³ | R⁵ | (R⁶)ₒ |
|---|---|---|---|---|
| A-817 | methyl | methyl | 2-CH$_2$OCF$_3$ | — |
| A-818 | methyl | methyl | 3-CH$_2$OCF$_3$ | — |
| A-819 | methyl | methyl | 4-CH$_2$OCF$_3$ | — |
| A-820 | methyl | methyl | 2-CH$_2$OCH$_2$CF$_3$ | — |
| A-821 | methyl | methyl | 3-CH$_2$OCH$_2$CF$_3$ | — |
| A-822 | methyl | methyl | 4-CH$_2$OCH$_2$CF$_3$ | — |
| A-823 | methyl | methyl | 2-CH(CH$_3$)OCH$_3$ | — |
| A-824 | methyl | methyl | 3-CH(CH$_3$)OCH$_3$ | — |
| A-825 | methyl | methyl | 4-CH(CH$_3$)OCH$_3$ | — |
| A-826 | methyl | methyl | 2-CH(CH$_3$)OCH$_2$CH$_3$ | — |
| A-827 | methyl | methyl | 3-CH(CH$_3$)OCH$_2$CH$_3$ | — |
| A-828 | methyl | methyl | 4-CH(CH$_3$)OCH$_2$CH$_3$ | — |
| A-829 | methyl | methyl | 2-CH(CH$_3$)OCF$_3$ | — |
| A-830 | methyl | methyl | 3-CH(CH$_3$)OCF$_3$ | — |
| A-831 | methyl | methyl | 4-CH(CH$_3$)OCF$_3$ | — |
| A-832 | methyl | methyl | 2-CH(CH$_3$)OCH$_2$CF$_3$ | — |
| A-833 | methyl | methyl | 3-CH(CH$_3$)OCH$_2$CF$_3$ | — |
| A-834 | methyl | methyl | 4-CH(CH$_3$)OCH$_2$CF$_3$ | — |
| A-835 | methyl | methyl | 2-OCHF$_2$ | 3-methyl |
| A-836 | methyl | methyl | 2-OCHF$_2$ | 4-methyl |
| A-837 | methyl | methyl | 2-OCHF$_2$ | 5-methyl |
| A-838 | methyl | methyl | 2-OCHF$_2$ | 6-methyl |
| A-839 | methyl | methyl | 3-OCHF$_2$ | 2-methyl |
| A-840 | methyl | methyl | 3-OCHF$_2$ | 4-methyl |
| A-841 | methyl | methyl | 3-OCHF$_2$ | 5-methyl |
| A-842 | methyl | methyl | 3-OCHF$_2$ | 6-methyl |
| A-843 | methyl | methyl | 2-OCHF$_2$ | 3-F |
| A-844 | methyl | methyl | 2-OCHF$_2$ | 4-F |
| A-845 | methyl | methyl | 2-OCHF$_2$ | 5-F |
| A-846 | methyl | methyl | 2-OCHF$_2$ | 6-F |
| A-847 | methyl | methyl | 3-OCHF$_2$ | 2-F |
| A-848 | methyl | methyl | 3-OCHF$_2$ | 4-F |
| A-849 | methyl | methyl | 3-OCHF$_2$ | 5-F |
| A-850 | methyl | methyl | 3-OCHF$_2$ | 6-F |
| A-851 | methyl | methyl | 2-OCHF$_2$ | 3-Cl |
| A-852 | methyl | methyl | 2-OCHF$_2$ | 4-Cl |
| A-853 | methyl | methyl | 2-OCHF$_2$ | 5-Cl |
| A-854 | methyl | methyl | 2-OCHF$_2$ | 6-Cl |
| A-855 | methyl | methyl | 3-OCHF$_2$ | 2-Cl |
| A-856 | methyl | methyl | 3-OCHF$_2$ | 4-Cl |
| A-857 | methyl | methyl | 3-OCHF$_2$ | 5-Cl |
| A-858 | methyl | methyl | 3-OCHF$_2$ | 6-Cl |
| A-859 | methyl | methyl | 2-CH$_2$OCH$_3$ | 3-methyl |
| A-860 | methyl | methyl | 2-CH$_2$OCH$_3$ | 4-methyl |
| A-861 | methyl | methyl | 2-CH$_2$OCH$_3$ | 5-methyl |
| A-862 | methyl | methyl | 2-CH$_2$OCH$_3$ | 6-methyl |
| A-863 | methyl | methyl | 3-CH$_2$OCH$_3$ | 2-methyl |
| A-864 | methyl | methyl | 3-CH$_2$OCH$_3$ | 4-methyl |
| A-865 | methyl | methyl | 3-CH$_2$OCH$_3$ | 5-methyl |
| A-866 | methyl | methyl | 3-CH$_2$OCH$_3$ | 6-methyl |
| A-867 | methyl | methyl | 2-CH$_2$OCH$_3$ | 3-F |
| A-868 | methyl | methyl | 2-CH$_2$OCH$_3$ | 4-F |
| A-869 | methyl | methyl | 2-CH$_2$OCH$_3$ | 5-F |
| A-870 | methyl | methyl | 2-CH$_2$OCH$_3$ | 6-F |
| A-871 | methyl | methyl | 3-CH$_2$OCH$_3$ | 2-F |
| A-872 | methyl | methyl | 3-CH$_2$OCH$_3$ | 4-F |
| A-873 | methyl | methyl | 3-CH$_2$OCH$_3$ | 5-F |
| A-874 | methyl | methyl | 3-CH$_2$OCH$_3$ | 6-F |
| A-875 | methyl | methyl | 2-CH$_2$OCH$_3$ | 3-Cl |
| A-876 | methyl | methyl | 2-CH$_2$OCH$_3$ | 4-Cl |
| A-877 | methyl | methyl | 2-CH$_2$OCH$_3$ | 5-Cl |
| A-878 | methyl | methyl | 2-CH$_2$OCH$_3$ | 6-Cl |
| A-879 | methyl | methyl | 3-CH$_2$OCH$_3$ | 2-Cl |
| A-880 | methyl | methyl | 3-CH$_2$OCH$_3$ | 4-Cl |
| A-881 | methyl | methyl | 3-CH$_2$OCH$_3$ | 5-Cl |
| A-882 | methyl | methyl | 3-CH$_2$OCH$_3$ | 6-Cl |
| A-883 | methyl | methyl | 2-CF$_3$ | 3-F |
| A-884 | methyl | methyl | 2-CF$_3$ | 4-F |
| A-885 | methyl | methyl | 2-CF$_3$ | 5-F |
| A-886 | methyl | methyl | 2-CF$_3$ | 6-F |
| A-887 | methyl | methyl | 3-CF$_3$ | 2-F |
| A-888 | methyl | methyl | 3-CF$_3$ | 4-F |
| A-889 | methyl | methyl | 3-CF$_3$ | 5-F |
| A-890 | methyl | methyl | 3-CF$_3$ | 6-F |
| A-891 | ethyl | methyl | 2-OCHF$_2$ | — |
| A-892 | ethyl | methyl | 3-OCHF$_2$ | — |
| A-893 | ethyl | methyl | 4-OCHF$_2$ | — |
| A-894 | ethyl | methyl | 2-OCF$_3$ | — |
| A-895 | ethyl | methyl | 3-OCF$_3$ | — |
| A-896 | ethyl | methyl | 4-OCF$_3$ | — |
| A-897 | ethyl | methyl | 2-CF$_3$ | — |
| A-898 | ethyl | methyl | 3-CF$_3$ | — |
| A-899 | ethyl | methyl | 4-CF$_3$ | — |
| A-900 | ethyl | methyl | 2-CH$_2$OCH$_3$ | — |
| A-901 | ethyl | methyl | 3-CH$_2$OCH$_3$ | — |
| A-902 | ethyl | methyl | 4-CH$_2$OCH$_3$ | — |
| A-903 | ethyl | methyl | 2-CH$_2$OCH$_2$CH$_3$ | — |
| A-904 | ethyl | methyl | 3-CH$_2$OCH$_2$CH$_3$ | — |
| A-905 | ethyl | methyl | 4-CH$_2$OCH$_2$CH$_3$ | — |
| A-906 | ethyl | methyl | 2-CH$_2$OCF$_3$ | — |
| A-907 | ethyl | methyl | 3-CH$_2$OCF$_3$ | — |
| A-908 | ethyl | methyl | 4-CH$_2$OCF$_3$ | — |
| A-909 | ethyl | methyl | 2-CH$_2$OCH$_2$CF$_3$ | — |
| A-910 | ethyl | methyl | 3-CH$_2$OCH$_2$CF$_3$ | — |
| A-911 | ethyl | methyl | 4-CH$_2$OCH$_2$CF$_3$ | — |
| A-912 | ethyl | methyl | 2-CH(CH$_3$)OCH$_3$ | — |
| A-913 | ethyl | methyl | 3-CH(CH$_3$)OCH$_3$ | — |
| A-914 | ethyl | methyl | 4-CH(CH$_3$)OCH$_3$ | — |
| A-915 | ethyl | methyl | 2-CH(CH$_3$)OCH$_2$CH$_3$ | — |
| A-916 | ethyl | methyl | 3-CH(CH$_3$)OCH$_2$CH$_3$ | — |
| A-917 | ethyl | methyl | 4-CH(CH$_3$)OCH$_2$CH$_3$ | — |
| A-918 | ethyl | methyl | 2-CH(CH$_3$)OCF$_3$ | — |
| A-919 | ethyl | methyl | 3-CH(CH$_3$)OCF$_3$ | — |
| A-920 | ethyl | methyl | 4-CH(CH$_3$)OCF$_3$ | — |
| A-921 | ethyl | methyl | 2-CH(CH$_3$)OCH$_2$CF$_3$ | — |
| A-922 | ethyl | methyl | 3-CH(CH$_3$)OCH$_2$CF$_3$ | — |
| A-923 | ethyl | methyl | 4-CH(CH$_3$)OCH$_2$CF$_3$ | — |
| A-924 | ethyl | methyl | 2-OCHF$_2$ | 3-methyl |
| A-925 | ethyl | methyl | 2-OCHF$_2$ | 4-methyl |
| A-926 | ethyl | methyl | 2-OCHF$_2$ | 5-methyl |
| A-927 | ethyl | methyl | 2-OCHF$_2$ | 6-methyl |
| A-928 | ethyl | methyl | 3-OCHF$_2$ | 2-methyl |
| A-929 | ethyl | methyl | 3-OCHF$_2$ | 4-methyl |
| A-930 | ethyl | methyl | 3-OCHF$_2$ | 5-methyl |
| A-931 | ethyl | methyl | 3-OCHF$_2$ | 6-methyl |
| A-932 | ethyl | methyl | 2-OCHF$_2$ | 3-F |
| A-933 | ethyl | methyl | 2-OCHF$_2$ | 4-F |
| A-934 | ethyl | methyl | 2-OCHF$_2$ | 5-F |
| A-935 | ethyl | methyl | 2-OCHF$_2$ | 6-F |
| A-936 | ethyl | methyl | 3-OCHF$_2$ | 2-F |
| A-937 | ethyl | methyl | 3-OCHF$_2$ | 4-F |
| A-938 | ethyl | methyl | 3-OCHF$_2$ | 5-F |
| A-939 | ethyl | methyl | 3-OCHF$_2$ | 6-F |
| A-940 | ethyl | methyl | 2-OCHF$_2$ | 3-Cl |
| A-941 | ethyl | methyl | 2-OCHF$_2$ | 4-Cl |
| A-942 | ethyl | methyl | 2-OCHF$_2$ | 5-Cl |
| A-943 | ethyl | methyl | 2-OCHF$_2$ | 6-Cl |
| A-944 | ethyl | methyl | 3-OCHF$_2$ | 2-Cl |
| A-945 | ethyl | methyl | 3-OCHF$_2$ | 4-Cl |
| A-946 | ethyl | methyl | 3-OCHF$_2$ | 5-Cl |
| A-947 | ethyl | methyl | 3-OCHF$_2$ | 6-Cl |
| A-948 | ethyl | methyl | 2-CH$_2$OCH$_3$ | 3-methyl |
| A-949 | ethyl | methyl | 2-CH$_2$OCH$_3$ | 4-methyl |
| A-950 | ethyl | methyl | 2-CH$_2$OCH$_3$ | 5-methyl |
| A-951 | ethyl | methyl | 2-CH$_2$OCH$_3$ | 6-methyl |
| A-952 | ethyl | methyl | 3-CH$_2$OCH$_3$ | 2-methyl |
| A-953 | ethyl | methyl | 3-CH$_2$OCH$_3$ | 4-methyl |
| A-954 | ethyl | methyl | 3-CH$_2$OCH$_3$ | 5-methyl |
| A-955 | ethyl | methyl | 3-CH$_2$OCH$_3$ | 6-methyl |
| A-956 | ethyl | methyl | 2-CH$_2$OCH$_3$ | 3-F |
| A-957 | ethyl | methyl | 2-CH$_2$OCH$_3$ | 4-F |
| A-958 | ethyl | methyl | 2-CH$_2$OCH$_3$ | 5-F |
| A-959 | ethyl | methyl | 2-CH$_2$OCH$_3$ | 6-F |
| A-960 | ethyl | methyl | 3-CH$_2$OCH$_3$ | 2-F |
| A-961 | ethyl | methyl | 3-CH$_2$OCH$_3$ | 4-F |
| A-962 | ethyl | methyl | 3-CH$_2$OCH$_3$ | 5-F |
| A-963 | ethyl | methyl | 3-CH$_2$OCH$_3$ | 6-F |
| A-964 | ethyl | methyl | 2-CH$_2$OCH$_3$ | 3-Cl |
| A-965 | ethyl | methyl | 2-CH$_2$OCH$_3$ | 4-Cl |
| A-966 | ethyl | methyl | 2-CH$_2$OCH$_3$ | 5-Cl |
| A-967 | ethyl | methyl | 2-CH$_2$OCH$_3$ | 6-Cl |
| A-968 | ethyl | methyl | 3-CH$_2$OCH$_3$ | 2-Cl |
| A-969 | ethyl | methyl | 3-CH$_2$OCH$_3$ | 4-Cl |
| A-970 | ethyl | methyl | 3-CH$_2$OCH$_3$ | 5-Cl |
| A-971 | ethyl | methyl | 3-CH$_2$OCH$_3$ | 6-Cl |
| A-972 | ethyl | methyl | 2-CF$_3$ | 3-F |

TABLE A-continued

| No. | R¹ | R³ | R⁵ | $(R^6)_o$ |
|---|---|---|---|---|
| A-973 | ethyl | methyl | 2-$CF_3$ | 4-F |
| A-974 | ethyl | methyl | 2-$CF_3$ | 5-F |
| A-975 | ethyl | methyl | 2-$CF_3$ | 6-F |
| A-976 | ethyl | methyl | 3-$CF_3$ | 2-F |
| A-977 | ethyl | methyl | 3-$CF_3$ | 4-F |
| A-978 | ethyl | methyl | 3-$CF_3$ | 5-F |
| A-979 | ethyl | methyl | 3-$CF_3$ | 6-F |
| A-980 | 2-fluoroethyl | methyl | 2-$OCHF_2$ | — |
| A-981 | 2-fluoroethyl | methyl | 3-$OCHF_2$ | — |
| A-982 | 2-fluoroethyl | methyl | 4-$OCHF_2$ | — |
| A-983 | 2-fluoroethyl | methyl | 2-$OCF_3$ | — |
| A-984 | 2-fluoroethyl | methyl | 3-$OCF_3$ | — |
| A-985 | 2-fluoroethyl | methyl | 4-$OCF_3$ | — |
| A-986 | 2-fluoroethyl | methyl | 2-$CF_3$ | — |
| A-987 | 2-fluoroethyl | methyl | 3-$CF_3$ | — |
| A-988 | 2-fluoroethyl | methyl | 4-$CF_3$ | — |
| A-989 | 2-fluoroethyl | methyl | 2-$CH_2OCH_3$ | — |
| A-990 | 2-fluoroethyl | methyl | 3-$CH_2OCH_3$ | — |
| A-991 | 2-fluoroethyl | methyl | 4-$CH_2OCH_3$ | — |
| A-992 | 2-fluoroethyl | methyl | 2-$CH_2OCH_2CH_3$ | — |
| A-993 | 2-fluoroethyl | methyl | 3-$CH_2OCH_2CH_3$ | — |
| A-994 | 2-fluoroethyl | methyl | 4-$CH_2OCH_2CH_3$ | — |
| A-995 | 2-fluoroethyl | methyl | 2-$CH_2OCF_3$ | — |
| A-996 | 2-fluoroethyl | methyl | 3-$CH_2OCF_3$ | — |
| A-997 | 2-fluoroethyl | methyl | 4-$CH_2OCF_3$ | — |
| A-998 | 2-fluoroethyl | methyl | 2-$CH_2OCH_2CF_3$ | — |
| A-999 | 2-fluoroethyl | methyl | 3-$CH_2OCH_2CF_3$ | — |
| A-1000 | 2-fluoroethyl | methyl | 4-$CH_2OCH_2CF_3$ | — |
| A-1001 | 2-fluoroethyl | methyl | 2-$CH(CH_3)OCH_3$ | — |
| A-1002 | 2-fluoroethyl | methyl | 3-$CH(CH_3)OCH_3$ | — |
| A-1003 | 2-fluoroethyl | methyl | 4-$CH(CH_3)OCH_3$ | — |
| A-1004 | 2-fluoroethyl | methyl | 2-$CH(CH_3)OCH_2CH_3$ | — |
| A-1005 | 2-fluoroethyl | methyl | 3-$CH(CH_3)OCH_2CH_3$ | — |
| A-1006 | 2-fluoroethyl | methyl | 4-$CH(CH_3)OCH_2CH_3$ | — |
| A-1007 | 2-fluoroethyl | methyl | 2-$CH(CH_3)OCF_3$ | — |
| A-1008 | 2-fluoroethyl | methyl | 3-$CH(CH_3)OCF_3$ | — |
| A-1009 | 2-fluoroethyl | methyl | 4-$CH(CH_3)OCF_3$ | — |
| A-1010 | 2-fluoroethyl | methyl | 2-$CH(CH_3)OCH_2CF_3$ | — |
| A-1011 | 2-fluoroethyl | methyl | 3-$CH(CH_3)OCH_2CF_3$ | — |
| A-1012 | 2-fluoroethyl | methyl | 4-$CH(CH_3)OCH_2CF_3$ | — |
| A-1013 | 2-fluoroethyl | methyl | 2-$OCHF_2$ | 3-methyl |
| A-1014 | 2-fluoroethyl | methyl | 2-$OCHF_2$ | 4-methyl |
| A-1015 | 2-fluoroethyl | methyl | 2-$OCHF_2$ | 5-methyl |
| A-1016 | 2-fluoroethyl | methyl | 2-$OCHF_2$ | 6-methyl |
| A-1017 | 2-fluoroethyl | methyl | 3-$OCHF_2$ | 2-methyl |
| A-1018 | 2-fluoroethyl | methyl | 3-$OCHF_2$ | 4-methyl |
| A-1019 | 2-fluoroethyl | methyl | 3-$OCHF_2$ | 5-methyl |
| A-1020 | 2-fluoroethyl | methyl | 3-$OCHF_2$ | 6-methyl |
| A-1021 | 2-fluoroethyl | methyl | 2-$OCHF_2$ | 3-F |
| A-1022 | 2-fluoroethyl | methyl | 2-$OCHF_2$ | 4-F |
| A-1023 | 2-fluoroethyl | methyl | 2-$OCHF_2$ | 5-F |
| A-1024 | 2-fluoroethyl | methyl | 2-$OCHF_2$ | 6-F |
| A-1025 | 2-fluoroethyl | methyl | 3-$OCHF_2$ | 2-F |
| A-1026 | 2-fluoroethyl | methyl | 3-$OCHF_2$ | 4-F |
| A-1027 | 2-fluoroethyl | methyl | 3-$OCHF_2$ | 5-F |
| A-1028 | 2-fluoroethyl | methyl | 3-$OCHF_2$ | 6-F |
| A-1029 | 2-fluoroethyl | methyl | 2-$OCHF_2$ | 3-Cl |
| A-1030 | 2-fluoroethyl | methyl | 2-$OCHF_2$ | 4-Cl |
| A-1031 | 2-fluoroethyl | methyl | 2-$OCHF_2$ | 5-Cl |
| A-1032 | 2-fluoroethyl | methyl | 2-$OCHF_2$ | 6-Cl |
| A-1033 | 2-fluoroethyl | methyl | 3-$OCHF_2$ | 2-Cl |
| A-1034 | 2-fluoroethyl | methyl | 3-$OCHF_2$ | 4-Cl |
| A-1035 | 2-fluoroethyl | methyl | 3-$OCHF_2$ | 5-Cl |
| A-1036 | 2-fluoroethyl | methyl | 3-$OCHF_2$ | 6-Cl |
| A-1037 | 2-fluoroethyl | methyl | 2-$CH_2OCH_3$ | 3-methyl |
| A-1038 | 2-fluoroethyl | methyl | 2-$CH_2OCH_3$ | 4-methyl |
| A-1039 | 2-fluoroethyl | methyl | 2-$CH_2OCH_3$ | 5-methyl |
| A-1040 | 2-fluoroethyl | methyl | 2-$CH_2OCH_3$ | 6-methyl |
| A-1041 | 2-fluoroethyl | methyl | 3-$CH_2OCH_3$ | 2-methyl |
| A-1042 | 2-fluoroethyl | methyl | 3-$CH_2OCH_3$ | 4-methyl |
| A-1043 | 2-fluoroethyl | methyl | 3-$CH_2OCH_3$ | 5-methyl |
| A-1044 | 2-fluoroethyl | methyl | 3-$CH_2OCH_3$ | 6-methyl |
| A-1045 | 2-fluoroethyl | methyl | 2-$CH_2OCH_3$ | 3-F |
| A-1046 | 2-fluoroethyl | methyl | 2-$CH_2OCH_3$ | 4-F |
| A-1047 | 2-fluoroethyl | methyl | 2-$CH_2OCH_3$ | 5-F |
| A-1048 | 2-fluoroethyl | methyl | 2-$CH_2OCH_3$ | 6-F |
| A-1049 | 2-fluoroethyl | methyl | 3-$CH_2OCH_3$ | 2-F |
| A-1050 | 2-fluoroethyl | methyl | 3-$CH_2OCH_3$ | 4-F |
| A-1051 | 2-fluoroethyl | methyl | 3-$CH_2OCH_3$ | 5-F |
| A-1052 | 2-fluoroethyl | methyl | 3-$CH_2OCH_3$ | 6-F |
| A-1053 | 2-fluoroethyl | methyl | 2-$CH_2OCH_3$ | 3-Cl |
| A-1054 | 2-fluoroethyl | methyl | 2-$CH_2OCH_3$ | 4-Cl |
| A-1055 | 2-fluoroethyl | methyl | 2-$CH_2OCH_3$ | 5-Cl |
| A-1056 | 2-fluoroethyl | methyl | 2-$CH_2OCH_3$ | 6-Cl |
| A-1057 | 2-fluoroethyl | methyl | 3-$CH_2OCH_3$ | 2-Cl |
| A-1058 | 2-fluoroethyl | methyl | 3-$CH_2OCH_3$ | 4-Cl |
| A-1059 | 2-fluoroethyl | methyl | 3-$CH_2OCH_3$ | 5-Cl |
| A-1060 | 2-fluoroethyl | methyl | 3-$CH_2OCH_3$ | 6-Cl |
| A-1061 | 2-fluoroethyl | methyl | 2-$CF_3$ | 3-F |
| A-1062 | 2-fluoroethyl | methyl | 2-$CF_3$ | 4-F |
| A-1063 | 2-fluoroethyl | methyl | 2-$CF_3$ | 5-F |
| A-1064 | 2-fluoroethyl | methyl | 2-$CF_3$ | 6-F |
| A-1065 | 2-fluoroethyl | methyl | 3-$CF_3$ | 2-F |
| A-1066 | 2-fluoroethyl | methyl | 3-$CF_3$ | 4-F |
| A-1067 | 2-fluoroethyl | methyl | 3-$CF_3$ | 5-F |
| A-1068 | 2-fluoroethyl | methyl | 3-$CF_3$ | 6-F |

The compounds of formula IA and IB according to the invention are prepared in analogy with methods known in the art. An important approach to the compounds according to the invention wherein $X^1$ is $NR^4$ is the reaction of a compound 1 with chlorosulfonic acid and subsequent reaction of the intermediate sulfonyl chloride 2 with an aniline derivative 3 as depicted in scheme 1. In scheme 1, $R^a$ is a nitrogen protecting group or $C_1$-$C_4$-alkyl. Suitable N-protecting groups are described, for example, in P. J. Kocienski "Protecting Groups", $2^{nd}$ ed., Georg Thieme Verlag, Stuttgart 2000, pp 186-237 and in the literature cited therein. Preferred examples of N-protecting groups are e.g. oxycarbonyl groups such as $C_1$-$C_6$-alkoxycarbonyl, e.g. methoxycarbonyl, ethoxycarbonyl and Boc (tert-butoxycarbonyl) and other oxycarbonyl groups such as benzyloxycarbonyl (Cbz), allyloxycarbonyl, 9-fluorenylmethoxycarbonyl (Fmoc) and 2-trimethylsilylethoxycarbonyl (Teoc), or 2-propenyl(allyl). Especially preferred for introduction of a sulfonylchloride group is the trifluoroacetyl group as a protecting group for the heterocyclyl nitrogen ring atom.

The reaction of compound 2 with 3 in scheme 1 takes place under the reaction conditions which are customary for preparing arylsulfonamide compounds, and which are described, for example, in J. March, Advanced Organic Chemistry, $3^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108.

The reaction is customarily carried out in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of compound 2 with compound 3 is customarily carried out in the presence of an auxiliary base. Suitable bases are inorganic bases, such as sodium carbonate or potassium carbonate, or sodium hydrogen carbonate or potassium hydrogen carbonate, and organic bases, for example trialkylamines, such as triethylamine, or pyridine compounds, such as pyridine, lutidine, 4-dimethylamino-pyridine and the like. The latter compounds can at the same time serve as solvents. The auxiliary base is customarily employed in at least equimolar quantities, based on the compound 1.

The reaction of compound 2 with compound 3 yields compound I' which, in case R$^a$ is an N-protecting group, is deprotected to yield the compound of the general formula IA (or IB; see below), wherein R$^1$ is hydrogen. Deprotection of the compound I' can be achieved by standard methods, e.g. by the methods as described in P. J. Kocienski "Protecting Groups", 2$^{nd}$ ed., Georg Thieme Verlag, Stuttgart 2000, pp 186-237 and in the literature cited therein, e.g. hydrolytically or hydrogenolytically, to give compounds IA/IB wherein R$^1$ is H.

Customary methods can then be used to react these compounds with an alkylating agent such as methyl iodide or dimethyl sulfate resulting in a compound of the formula IA/IB, in which R$^1$ is C$_1$-C$_4$-alkyl. The reaction conditions which are required for this alkylating reaction are disclosed, for example, in WO 02/083652, Tetrahedron 2000, 56(38) pp. 7553-7560 and Synlett. 2000 (4), pp. 475-480.

For preparing a compound of formula IA/IB, in which X$^1$ or X$^2$ is NR$^4$ and R$^1$ is methyl, it is likewise possible to react a compound of formula I, in which R$^1$ is hydrogen, with formaldehyde in the presence of a reducing agent in a sense of a reductive amination. Suitable reducing agents are borohydrides such as sodium borohydride, sodium cyanoborohydride, sodium triacetoxyborohydride or borane-pyridine. The reductive amination is usually carried out in an organic solvent such as dichloromethane, 1,2-dichloroethane, tetrahydrofuran or acetonitrile.

Reaction of the compound I' with an alkylating agent yields a compound of the formula I', wherein R$^4$ is C$_1$-C$_4$-alkyl.

Scheme 1:

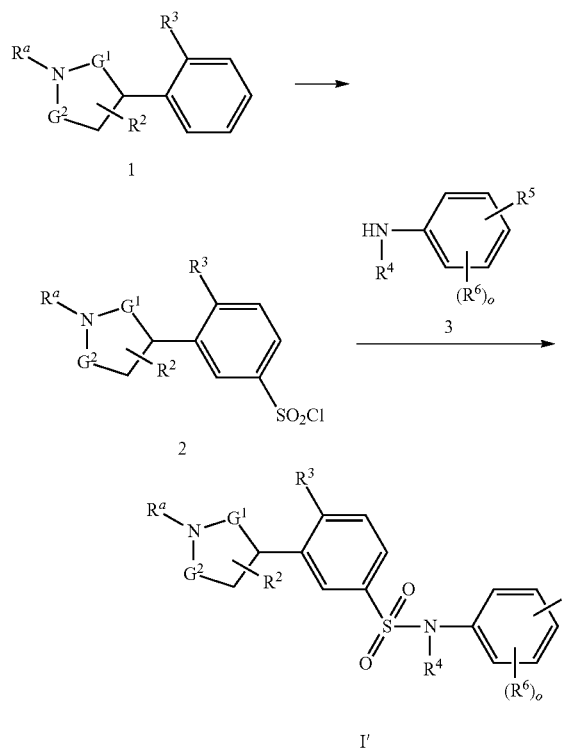

Compounds of the formula I', wherein R$^a$ is a nitrogen protecting group, in particular trifluoroacetyl, a C$_1$-C$_6$-alkoxycarbonyl group such as methoxycarbonyl, ethoxycarbonyl and Boc (tert-butoxycarbonyl), are novel and thus form also part of the present invention.

The reaction sequence for the preparation of sulfonamides (compounds of the invention wherein X$^1$ or X$^2$ is NR$^4$) is shown in scheme 1 above for compounds IA, but applies analogously to sulfonamide compounds IB (compounds IB wherein X$^2$ is NR$^4$).

The compounds 1 are either commercially available or can be prepared by routes known in the art, e.g. as described in WO 2007/118899.

For instance, the pyrrolidine compound 1 (G$^1$, G$^2$=CH$_2$) wherein R$^2$ is bound in 4-position can be prepared by a [3+2] dipolar cycloaddition of a non-stabilized azomethine ylid to a 1-alkenylaryl or hetaryl derivative 4 (e.g. a vinyl benzene, R$^2$=H) as shown in scheme 2 below. This procedure is generally described in J. Org. Chem. 1987, 52, 235. The precursor of the ylid, the amine N(CH$_2$R$^a$)(CH$_2$SiMe$_3$)(CH$_2$OCH$_3$) (5), is commercially available or can be synthesized from NH$_2$(CH$_2$R$^a$), Me$_3$SiCH$_2$Cl and HCHO in the presence of methanol.

Scheme 2

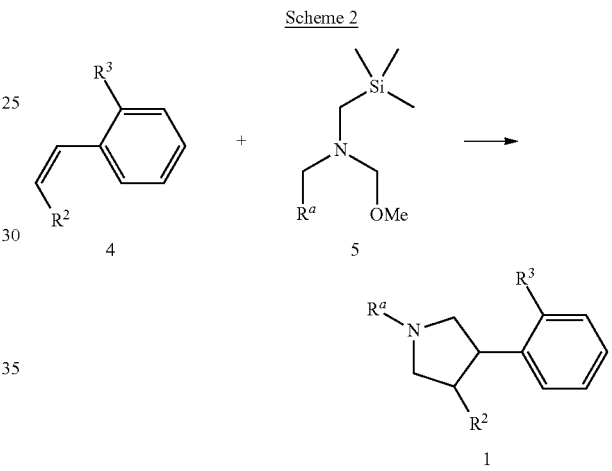

The 1-alkenyl-(hetero)aromatic compound 4 can be synthesized e.g. by a Stille coupling of a halogeno benzene, e.g. a bromo benzene, with the corresponding alkenyl tributyl stannate, such as vinyl or isobutenyl tributyl stannate, in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). By choosing a special Stille isomer (e.g. cis- or trans-isobutenyl tributyl stannate), the corresponding cis- or trans alkyl phenyl pyrrolidine can be prepared selectively.

Alternatively, the 1-alkenyl-(hetero)aromatic compound 4 can be synthesized by a Wittig reaction of aryl aldehyde with a Wittig reagent such as PPh$_3$=CHR(R is H, or C$_1$-C$_3$-alkyl). Conditions for the Wittig reaction are well known in the art and are, e.g. discussed in Jerry March, Advanced Organic Chemistry, John Wiley, 3$^{rd}$ edition, page 845 ff.

The pyrrolidine compound 1 (G$^1$, G$^2$=CH$_2$) wherein R$^2$ is H can also be prepared by a [3+2] dipolar cycloaddition of a non-stabilized azomethine ylid to a 1-alkynylbenzene 6 (see, e.g., Tetrahedron 1996, 52, 59), as shown in scheme 3 below. The resulting pyrroline 7 is then hydrogenated to the corresponding pyrrolidine 1. If the hydrogenation is carried out under chiral conditions, e.g. by using chiral catalysts, the enantiomerically pure phenylpyrrolidine compounds can be obtained. Chiral hydrogenation catalysts are well known in the art.

Scheme 3

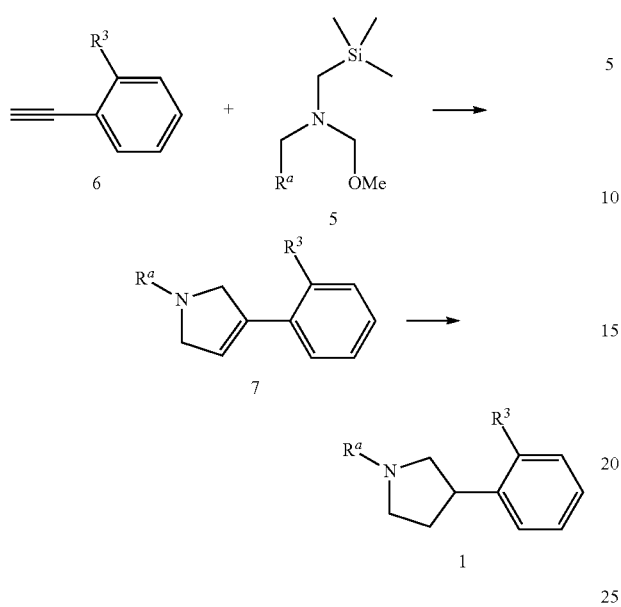

The pyrrolidine compound 1 (G$^1$, G$^2$=CH$_2$) wherein R$^2$ is H can also be prepared by a metal catalyzed reaction of an aryl halide 8 (preferably iodide) with a commercially available boronic acid ester derivative 9 (as described, for example, in Synlett (5), 829-831 (2002); Angew. Chem. Int. ed. 39(6), 1066 (2000); or in the references cited therein) as shown in scheme 4 below where R$^a$ is e.g. a tert-butyloxycarbonyl group. The resulting pyrroline 7 is then hydrogenated to the corresponding pyrrolidine 1. If the hydrogenation is carried out under chiral conditions, e.g. by using chiral catalysts, the enantiomerically pure phenylpyrrolidine compounds can be obtained. Chiral hydrogenation catalysts are well known in the art.

Scheme 4

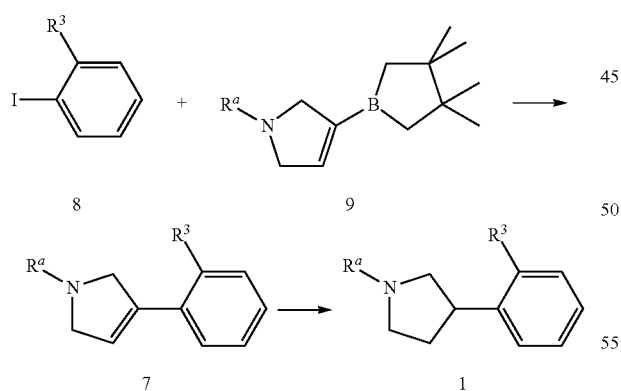

Piperidine compounds (either G$^1$ or G$^2$ is CH$_2$CH$_2$) can be prepared accordingly.

Aniline compounds 3 are either commercially available or can be prepared by known synthetic routes.

Compounds having a bridged bicyclic [3,1,0] or [4,1,0] system (i.e. compounds IB) can be prepared from vinyl esters as depicted in scheme 5, followed by further modification of compounds 15 as described in Scheme 1.

Scheme 5

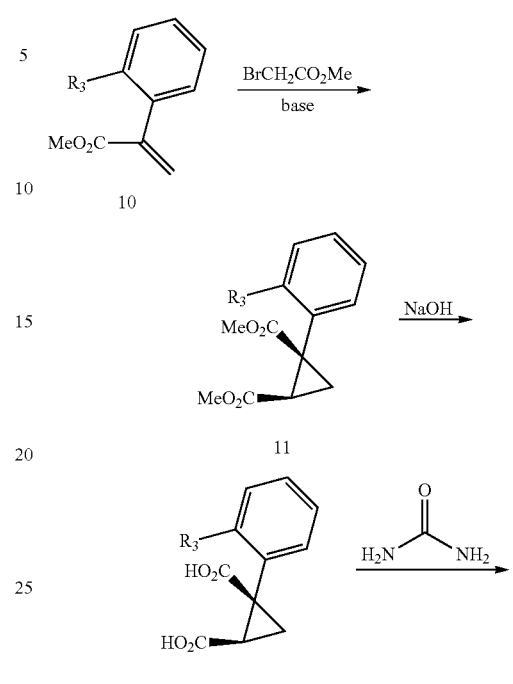

An alternative approach is reacting compounds 17 with a carbene generating system to yield compounds 13 (scheme 6, Synthesis, Stuttgart (14), 2284-2286 (2005); U.S. Pat. No. 4,544,665; US 20090326011).

Scheme 6

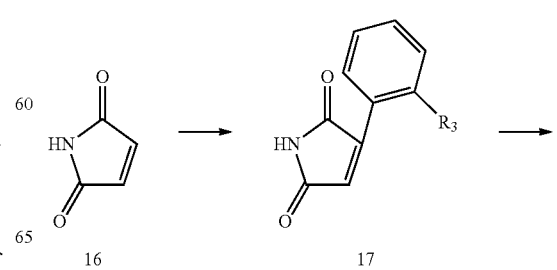

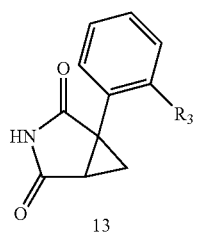

Sulfone compounds of the present invention where $X^1$ is a bond can be prepared according to schemes 7 and 8, either from compounds 19 (which in turn can be prepared from aniline compounds 18 where the $NH_2$ group is transformed into a group $X^3$ which can either be e.g. iodine or bromine, via a Sandmeyer reaction) by reaction with a thio-phenol compound 20 and subsequent oxidation of the sulfide (scheme 7) with suitable oxidizing agents such as oxone or peracids, or by reaction of a compound 19 with the salt of a sulfinic acid derivative 21 (usually the sodium salt) without the further need for an oxidative step (scheme 8; e.g. Synlett, 2003, 361). In this case, compounds of formula I″ can be prepared by the palladium-catalyzed reaction of the sulfinic acid salt 21 with compounds 19, wherein $X^3$ is bromine or iodine. A suitable palladium catalyst is tris(dibenzylideneacetone)dipalladium (0) $(Pd_2(dba)_3)$. The sulfone I″ is usually prepared in the presence of Xantphos, a rigid bidendate ligand. The reaction is also usually carried out in the presence of n-tetrabutylammonium chloride.

Scheme 7:

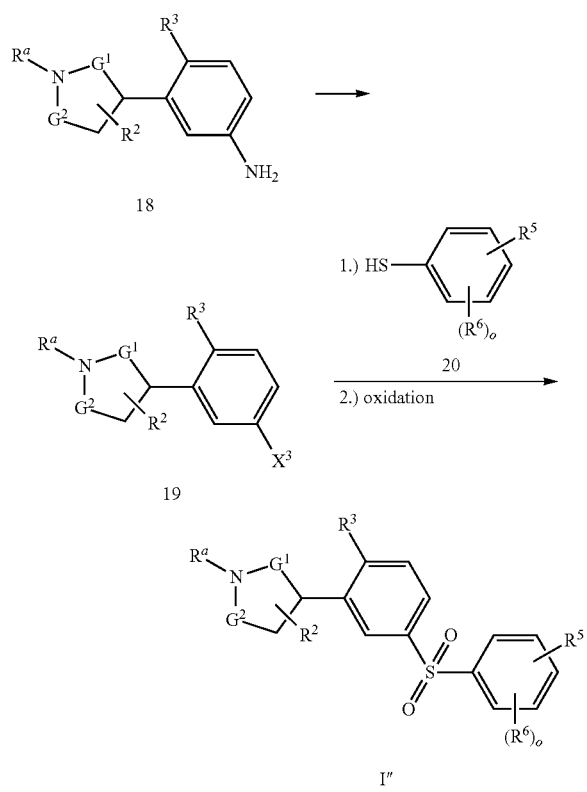

Scheme 8:

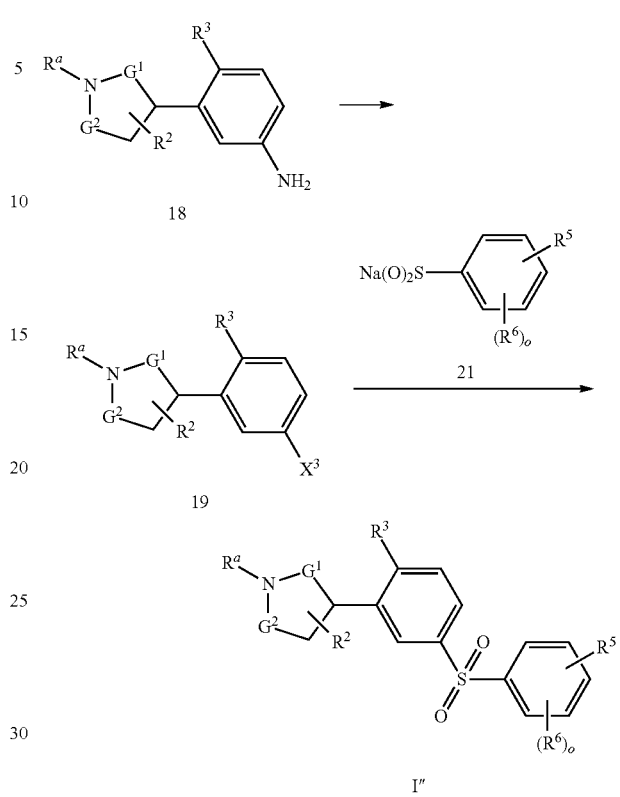

The reaction sequence for the preparation of sulfones (compounds of the invention wherein $X^1$ is a bond) is shown in schemes 7 and 8 above for compounds IA, but applies analogously to sulfone compounds IB (compounds IB wherein $X^2$ is a bond).

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", AndréLoupy (Ed.), Wiley-VCH 2002.

The acid addition salts of compounds IA or IB are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The present invention moreover relates to compounds of formula IA and IB as defined above, wherein at least one of the atoms has been replaced by its stable, non-radioactive isotope (e.g., hydrogen by deuterium, $^{13}C$ by $^{13}C$, $^{14}N$ by $^{15}N$, $^{16}O$ by $^{18}O$) and preferably wherein at least one hydrogen atom has been replaced by a deuterium atom.

Of course, the compounds according to the invention contain more of the respective isotope than this naturally occurs and thus is anyway present in the compounds IA or IB.

Stable isotopes (e.g., deuterium, $^{13}$C, $^{15}$N, $^{18}$O) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogen atoms present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The present invention further relates to a pharmaceutical composition comprising at least one compound of formula IA and/or IB, a stereoisomer, prodrug, tautomer and/or physiologically tolerated acid addition salt thereof and optionally at least one physiologically acceptable carrier and/or auxiliary substance.

The invention relates moreover to the use of compounds of formula IA and/or IB or of a stereoisomer, N-oxide, prodrug, tautomer or physiologically tolerated acid addition salt thereof or of a compound of formula IA and/or IB, wherein at least one of the atoms has been replaced by its stable, non-radioactive isotope, for the preparation of a medicament for the treatment of a medical disorder susceptible to the treatment with a 5-$HT_6$ receptor ligand, and to a method for treating a medical disorder susceptible to the treatment with a 5-$HT_6$ receptor ligand, said method comprising administering an effective amount of at least one compound of formula IA and/or IB or of a stereoisomer, N-oxide, prodrug, tautomer or physiologically tolerated acid addition salt thereof or of a compound of formula IA and/or IB, wherein at least one of the atoms has been replaced by its stable, non-radioactive isotope, or of a pharmaceutical composition as defined above to a subject in need thereof.

The present invention also relates to the compounds of formula IA and/or IB or a stereoisomer, N-oxide, prodrug, tautomer or physiologically tolerated acid addition salt thereof or a compound of formula IA and/or IB, wherein at least one of the atoms has been replaced by its stable, non-radioactive isotope, for use in modulating the 5-$HT_6$ receptor.

The compounds of the present invention can be a 5-$HT_6$ receptor agonist, including partial agonistic activity, or a 5-$HT_6$ receptor antagonist, including inverse agonist activity.

The compounds according to the present invention, as well as their salts and their N-oxides, have a surprisingly high affinity for 5-$HT_6$ receptors. The high affinity of the compounds according to the invention for 5-$HT_6$ receptors is reflected in very low in-vitro receptor binding constants ($K_i$ (5-$HT_6$) values) of as a rule less than 500, 100 or 50 nM (nmol/l), preferably of less than 10 nM and, in particular of less than 5 nM. The displacement of $^3$H-LSD can, for example, be used in receptor binding studies for determining binding affinities to 5-$HT_6$ receptors.

Furthermore the compounds of the invention, as well as their salts and their N-oxides, are highly selective 5-$HT_6$ receptor ligands which, because of their low affinity for other receptors such as dopamine receptors, adrenergic receptors, muscarinic receptors, histamine receptors, opiate receptors, in particular dopamine $D_2$, $\alpha_1$-adrenergic and histamine $H_1$ receptors, give rise to fewer side-effects than other, less selective 5-$HT_6$ ligands.

For instance the 5-$HT_6$/$D_2$, 5-$HT_6$/$\alpha_1$-adrenergic or 5-$HT_6$/$H_1$ selectivities of the compounds according to the present invention, i.e. the ratios $K_i(D_2)/K_i(5-HT_6)$, $K_i(\alpha_1$-adrenergic$)/K_i(5-HT_6)$ or $K_i(H_1)/K_i(5-HT_6)$ of the receptor binding constants, is as a rule at least 25, preferably at least 50, even better at least 100.

The displacement of [$^3$H]SCH23390 or [$^{125}$I]spiperone can be used, for example, for carrying out receptor binding studies on $D_1$, $D_2$ and $D_4$ receptors.

Furthermore the compounds of the present invention because of their structural features are susceptible to display an enhanced brain penetration than other known 5-$HT_6$ receptor ligands.

Moreover, the compounds of the present invention because of their structural features show no or only low blockade of the hERG channel.

Because of their binding profile, the compounds of the present invention can be used for treating diseases which respond to 5-$HT_6$ receptor ligands (or which are susceptible to treatment with a 5-$HT_6$ receptor ligand), i.e. they are effective for treating those medical disorders or diseases in which exerting an influence on (modulating) the 5-$HT_6$ receptor leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-$HT_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases including e.g. drug addiction and obesity.

The addiction diseases include psychic disorders and behavioral disturbances which are caused by the abuse of psychotropic substances, including certain pharmaceuticals, such as sedative, anxiolytica, hypnotics or narcotics (hereinafter also referred to as drug addiction), and also other addiction diseases, such as addiction to gaming (gambling; impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, hallucinogens, NMDA-receptor antagonists such phencyclidine and related cyclidines, dextrometorphan, dextrorphan, ibogaine, ketimine and tiletamine, cannabis, nicotine and alcohol. Other addiction diseases include gaming (gambling), including problem gambling (compulsive gambling, ludomania), computer or video game addiction and internet addiction.

With regard to the treatment of addiction diseases, particular preference is given to those compounds according to the present invention which themselves do not possess any psychotropic effect. This can also be observed in a test using rats, which, after having been administered compounds which can be used in accordance with the invention, reduce their self administration of psychotropic substances, for example cocaine or alcohol.

According to another aspect of the present invention, the compounds according to the invention are suitable for treating disorders whose causes can at least partially be attributed to an anomalous activity of $5\text{-HT}_6$ receptors.

According to another aspect of the present invention, the treatment is directed, in particular, toward those disorders which can be influenced, within the sense of an expedient medicinal treatment, by the binding of preferably exogeneously administered binding partners (ligands) to $5\text{-HT}_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of the present invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of the present invention are particularly suitable for treating addiction diseases caused for instance by the abuse of psychotropic substances, such as pharmaceuticals, narcotics, nicotine or alcohol, including psychic disorders and behavioral disturbances related thereto. The compounds of the present invention are likewise particularly suitable for treating addiction diseases which are not caused by the abuse of psychotropic substances, such as gaming (gambling), including problem gambling (compulsive gambling, ludomania), computer or video game addiction and internet addiction. With regard to addiction diseases, the compound of the present invention can be used for the therapy during addiction and also for preventing relapse into addiction.

According to another aspect of the invention the compounds of the invention, their salts and their N-oxides are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of the invention, their salts and/or their N-oxides are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants;

chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

EXAMPLES

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

I. Preparation of the Compounds I

Example 1

N-(2-Difluoromethoxy-5-methyl-phenyl)-4-methoxy-3-pyrrolidin-3-yl-benzenesulfonamide hydrochloride (corresponds to the compound of formula I.a, wherein the combination of $R^1$, $R^3$, $R^5$ and $(R^6)_o$ is as defined in row A-36 of table A)

1.1 2,2,2-Trifluoro-1-(3-(2-methoxyphenyl)pyrrolidin-1-yl)ethanone 3.08 g of 2,2,2-trifluoroacetic anhydride (14.67 mmol) were dissolved in 50 mL of dichloromethane, the solution was cooled to −20° C., and 2 g 3-(2-methoxyphenyl)-pyrrolidin (11.28 mmol, commercially available from Allweys) dissolved in 70 mL of dichloromethane added dropwise. The reaction mixture was allowed to slowly warm to room temperature and stirred 18 h at room temperature. After addition of 150 mL of ice water, the phases were separated and the organic layer washed twice with water, with a 1% aqueous sodium hydrogencarbonate solution, saturated aqueous sodium chloride solution, dried over sodium sulphate, filtered and the solvent evaporated under reduced pressure to yield 1.7 g of the title compound which was used in the subsequent step without further purification.

1.2 4-Methoxy-3-(1-(2,2,2-trifluoroacetyl)pyrrolidin-3-yl)benzene-1-sulfonyl chloride 1.7 g of 2,2,2-trifluoro-1-(3-(2-methoxyphenyl)pyrrolidin-1-yl)ethanone (6.22 mmol) were dissolved in 5 mL of dichloromethane and the solution was cooled to −5° C. At this temperature, 14.5 g of chlorosulfonic acid (124 mmol) were slowly added dropwise. Stirring was continued for 1 h at −5° C. and 18 h at room temperature. The reaction was then cooled to 0° C. and slowly added into 30 g of a water/ice mixture. The suspension was extracted 5 times with 100 mL of dichloromethane and the combined organic phases were washed twice with 5% aqueous sodium hydrogencarbonate solution. The organic layer was dried over sodium sulfate, filtered, and the solvent was evaporated to yield 2.1 g of the title compound as a yellowish solid (storage in the refrigerator under argon atmosphere).

1.3 N-(2-(difluoromethoxy)-5-methylphenyl)-4-methoxy-3-(1-(2,2,2 trifluoroacetyl)pyrrolidin-3-yl) benzenesulfonamide 0.093 g of 2-(difluoromethoxy)-5-methylaniline (0,538 mmol, purchased at Fluorochem) were dissolved in 10 mL of pyridin. 0.2 g of 4-methoxy-3-(1-(2,2,2-trifluoroacetyl)pyrrolidin-3-yl)benzene-1-sulfonyl chloride (0.538 mmol) were slowly added. The reaction mixture was stirred at room temperature for 18 h, and the solvent was evaporated and several times co-distilled with toluene. The oily brown residue was dissolved in dichloromethane and washed with a 5% aqueous ammonium chloride solution. After washing with saturated aqueous sodium chloride solution, the organic layer was dried over sodium sulphate, filtered, and the solvent evaporated. The crude product was purified via silica gel chromatography using a 40 g Redisep-column with dichloromethane/methanol 0-20% to yield 0.096 g of the title compound.

1.4 N-(2-Difluoromethoxy-5-methyl-phenyl)-4-methoxy-3-pyrrolidin-3-yl-benzenesulfonamide hydrochloride 0.096 g of N-(2-(difluoromethoxy)-5-methylphenyl)-4-methoxy-3-(1-(2,2,2 trifluoroacetyl)pyrrolidin-3-yl)benzenesulfonamide (0.189 mmol) were dissolved in methanol. 0.409 mL of 6 N aqueous NaOH (2.454 mmol) was added and the reaction stirred for 2 h at 20° C. Upon completion of the reaction, the solvent was evaporated, water added and the pH adjusted to neutral conditions by addition of saturated aqueous ammonium chloride solution. The aqueous phase was extracted with ethyl acetate and the combined organic fractions dried over sodium sulphate, filtered, and evaporated to dryness. The residue was dissolved in dichloromethane, 2 N HCl in diethyl ether added and the mixture evaporated. Water was added and the solution extracted three times with dichloromethane. The aqueous phase was lyophilized to yield 0.07 g of the title compound.

ESI-MS: 413.1 [M+H]$^+$ $^1$H-NMR (DMSO-$d_6$, 400 Hz): δ [ppm] 9.7 (broad, 1H), 9.44 (broad 2H), 7.67 (s, 1H), 7.64 (d, 1H), 7.15 (d, 1H), 7.11 (s, 1H), 6.95-7.05 (m, 2H), 6.88 (t, 1H, C$\underline{H}$F$_2$), 3.88 (s, 3H), 3.61 (m, 1H), 3.54 (m, 1H), 3.35 (m, 1H), 3.22 (m, 1H), 2.95 (m, 1H), 2.22 (s, 3H), 2.18 (m, 1H), 1.90 (m, 1H).

Example 2

N-(2-Difluoromethoxy-5-methyl-phenyl)-4-methoxy-3-(1-methyl-pyrrolidin-3-yl)-benzenesulfonamide hydrochloride (corresponds to the compound of formula I.a, wherein the combination of $R^1$, $R^3$, $R^5$ and $(R^6)_o$ is as defined in row A-125 of table A)

To a solution of 0.045 g of N-(2-difluoromethoxy-5-methyl-phenyl)-4-methoxy-3-pyrrolidin-3-yl-benzenesulfonamide (0.109 mmol) in 5 mL of acetonitrile, 0.024 mL of an 37% aqueous formaldehyde solution (0.327 mmol) and 0.089 g of sodium cyanoborohydride (0.142 mmol) were added. Aqueous 0.1 N hydrochloride acid was added to keep the pH at 2. The reaction was stirred for 18 h at room temperature, quenched with water and evaporated to dryness under vacuum. The residue was partitioned between ethyl acetate and water, washed with an 5% aqueous sodium hydrogencarbonate solution and saturated aqueous sodium chloride solution, and the organic layer dried over sodium sulphate and filtered. The solvent was evaporated under vacuum. The crude product was purified via silica gel chromatography with a 2 g Chromabond NP cartridge (dichloromethane/methanol 0-5%) and further transferred into the hydrochloride salt through addition of 2 N hydrochlorid acid in diethyl ether. After extraction with dichloromethane, and lyophilisation of the aqueous layer 0.0073 g of the title compound were obtained.

ESI-MS: 427.1 $[M+H]^+$

Example 3

4-Methoxy-N-(2-methoxymethyl-phenyl)-3-pyrrolidin-3-yl-benzenesulfonamide hydrochloride (corresponds to the compound of formula I.a, wherein the combination of $R^1$, $R^3$, $R^5$ and $(R^6)_o$ is as defined in row A-10 of table A)

0.013 g of the product were obtained by the method as described for Example 1.

ESI-MS: 377.1 $[M+H]^+$

Example 4

N-(2-Difluoromethoxy-5-methyl-phenyl)-4-methoxy-3-piperidin-4-yl-benzenesulfonamide hydrochloride (corresponds to the compound of formula I.m, wherein the combination of $R^1$, $R^3$, $R^5$ and $(R^6)_o$ is as defined in row A-36 of table A)

0.008 g of the product were obtained by the method as described for Example 1 starting from 4-(2-methoxy-phenyl)-piperidine.

ESI-MS: 427.1 $[M+H]^+$

Example 5

N-(2-Difluoromethoxy-4-methyl-phenyl)-4-methoxy-3-piperidin-4-yl-benzenesulfonamide hydrochloride (corresponds to the compound of formula I.m, wherein the combination of $R^1$, $R^3$, $R^5$ and $(R^6)_o$ is as defined in row A-35 of table A)

0.113 g of the product were obtained by the method as described for Example 1 starting from 4-(2-methoxy-phenyl)-piperidine.

ESI-MS: 427.1 $[M+H]^+$

Example 6

4-Methoxy-N-(2-methoxymethyl-phenyl)-3-piperidin-4-yl-benzenesulfonamide hydrochloride (corresponds to the compound of formula I.m, wherein the combination of $R^1$, $R^3$, $R^5$ and $(R^6)_o$ is as defined in row A-10 of table A)

0.116 g of the product were obtained by the method as described for Example 1 starting from 4-(2-methoxy-phenyl)-piperidine.

ESI-MS: 391.1 $[m+H]^+$

Example 7

N-(2-Difluoromethoxy-5-methyl-phenyl)-4-methoxy-3-(1-methyl-piperidin-4-yl)-benzenesulfonamide hydrochloride (corresponds to the compound of formula I.m, wherein the combination of $R^1$, $R^3$, $R^5$ and $(R^6)_o$ is as defined in row A-125 of table A)

0.159 g of the product were obtained by the method as described for Examples 1 and 2 starting from 4-(2-methoxyphenyl)-piperidine.

ESI-MS: 441.1 $[M+H]^+$

II. Biological Investigations

Displacement of radioligands binding to the following cloned human receptors
1. Preparation of Membranes by Ultrasonic Treatment and Differential Centrifugation Cells from stable clonal cell lines expressing the corresponding receptor (5-HT$_6$, $\alpha_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 μg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 μg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 μl in the presence of various concentrations of test compound ($10^{-5}$ M to $10^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96 well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a $K_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 μm pargyline, pH 7.4) to a concentration of 8 μg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 μM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

b) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM MgCl$_2$, 5 mM KCl, 1.5 mM CaCl$_2$, pH 7.4) to a concentration of 15 μg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 μM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

c) α$_1$-Adrenergic Receptor Binding Assay

CHO-K$_1$ cells stably expressing the α$_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 μg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

d) H$_1$ Receptor Binding Assay

CHO-K$_1$ cells stably expressing the histamine H$_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM Na$_2$HPO$_4$, 50 mM KH$_2$PO$_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). IC$_{50}$, nH and $K_i$ values were expressed as geometrical mean. For receptors with a low affinity for the test compound, where the highest tested compound concentration inhibited less than 30% of specific radioligand binding, $K_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-HT$_6$), $K_i$(D$_2$), $K_i$(α$_1$-adrenergic) and $K_i$(H$_1$), respectively, as described herein before, and given in table I.

In these tests, the compounds according to the invention exhibit very good affinities for the 5-HT$_6$ receptor ($K_i$<250 nM or <50 nM or <20 nM and frequently <10 nM). Furthermore those compounds bind selectively to the 5-HT$_6$ receptor, as compared to the affinity for the D$_2$, the α$_1$-adrenergic or the H$_1$ receptors. These compounds exhibit little affinities for the D$_2$, α$_1$-adrenergic or H$_1$ receptors ($K_i$>250 nM or >1000 nM and frequently >10000 nM).

Example 1: Ki (5HT$_6$)<10 nM
Example 2: Ki (5HT$_6$)<10 nM
Example 3: Ki (5HT$_6$)<20 nM
Example 4: Ki (5HT$_6$)<10 nM
Example 5: Ki (5HT$_6$)<20 nM
Example 6: Ki (5HT$_6$)<100 nM
Example 7: Ki (5HT$_6$)<10 nM 4. Determination of the Metabolic Stability The metabolic stability of the compounds of the invention was determined in the following assay by analyzing the microsomal half-life. The test substances are incubated in a concentration of 0.5 μM as follows:

0.5 μM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The remaining test compound concentrations are being determined by liquid chromatography—mass spectrometry analysis. Intrinsic clearance values are calculated using the elimination rate constant of test compound depletion.

We claim:
1. A compound of formula (IA)

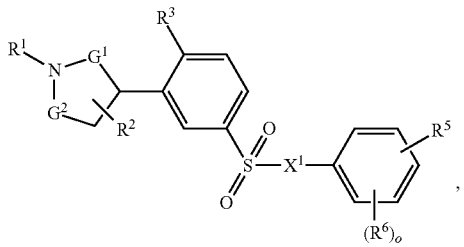

or a stereoisomer, tautomer, or a physiologically tolerated acid addition salt thereof,
wherein
$X^1$ is $NR^4$;
$R^1$ is selected from the group consisting of hydrogen, $C_1$-$C_4$-alkyl and fluorinated $C_1$-$C_4$-alkyl;
$R^2$ is selected from the group consisting of hydrogen and $C_1$-$C_4$-alkyl;
$R^3$ is selected from the group consisting of hydrogen, halogen, $C_1$-$C_4$-alkyl, fluorinated $C_1$-$C_4$-alkyl, $C_1$-$C_4$-alkoxy and fluorinated $C_1$-$C_4$-alkoxy;
$R^4$ is selected from the group consisting of hydrogen, $C_1$-$C_4$-alkyl and fluorinated $C_1$-$C_4$-alkyl;
$R^5$ is selected from the group consisting of $C_1$-$C_6$-hydroxyalkyl, $C_1$-$C_6$ alkoxy, $C_1$-$C_6$-hydroxyalkoxy, $C_1$-$C_6$-alkoxy-$C_1$-$C_6$-alkoxy, fluorinated $C_1$-$C_6$-alkoxy, fluorinated $C_1$-$C_6$-alkoxy-$C_1$-$C_6$-alkoxy, and a group -A-[O—B]$_p$—O—$R^7$;
where
A and B are independently of each other $C_1$-$C_4$-alkylene or fluorinated $C_1$-$C_4$-alkylene;
$R^7$ is $C_1$-$C_4$-alkyl or fluorinated $C_1$-$C_4$-alkyl;
p is 0, 1, 2, 3, 4, 5 or 6;
$R^6$ is selected from the group consisting of halogen, $C_1$-$C_2$-alkyl, fluorinated $C_1$-$C_2$-alkyl, $C_1$-$C_2$-alkoxy and fluorinated $C_1$-$C_2$-alkoxy;
$G^1$ is $CH_2$ or $CH_2CH_2$;
$G^2$ is $CH_2$ or $CH_2CH_2$;
o is 0, 1 or 2.
2. The compound of claim 1, where A is $C_1$-$C_2$-alkylene.
3. The compound of claim 2, where A is methylene ($CH_2$) or 1,1-ethylene [$CH(CH_3)$].
4. The compound of claim 1, where B is $C_2$-$C_3$-alkylene.
5. The compound of claim 1, where p is 0.
6. The compound of claim 1, where $R^7$ is $C_1$-$C_2$-alkyl or fluorinated $C_1$-$C_2$-alkyl.
7. The compound of claim 1, where $R^5$ is selected from the group consisting of fluorinated $C_1$-$C_2$-alkoxy, $C_1$-$C_2$-alkoxymethyl, 1-($C_1$-$C_2$-alkoxy)-ethyl, (fluorinated $C_1$-$C_2$-alkoxy)-methyl and 1-(fluorinated $C_1$-$C_2$-alkoxy)-ethyl.
8. The compound of claim 7, where $R^5$ is selected from the group consisting of fluoromethoxy, difluoromethoxy, trifluoromethoxy, methoxymethyl, ethoxymethyl, 2,2,2-trifluoroethoxymethyl and 1-methoxyethyl.
9. The compound of claim 8, where $R^5$ is selected from the group consisting of difluoromethoxy, methoxymethyl, ethoxymethyl, 2,2,2-trifluoroethoxymethyl and 1-methoxyethyl.
10. The compound of claim 1, where $R^5$ is bound in the 2- or 3-position, relative to the 1-position of the sulfonyl(amino) group $SO_2$—$X^1$.
11. The compound of claim 1, where $R^1$ is hydrogen or $C_1$-$C_4$ alkyl.
12. The compound of claim 1, where $R^2$ is hydrogen.
13. The compound of claim 1, where $R^3$ is selected from the group consisting of methoxy, ethoxy, methyl and ethyl.
14. The compound of claim 1, where $R^4$ is hydrogen or methyl.
15. The compound of claim 1, where $R^6$ is selected from the group consisting of F, Cl, methyl, difluoro-methyl, trifluoromethyl, methoxy, difluoromethoxy and trifluoromethoxy.
16. The compound of claim 1, where o is 0 or 1.
17. The compound of claim 1, where $G^1$ is $CH_2$ and $G^2$ is $CH_2$; or $G^1$ is $CH_2$ and $G^2$ is $CH_2CH_2$; or $G^1$ is $CH_2CH_2$ and $G^2$ is $CH_2$.
18. The compound of claim 1, where
$X^1$ is NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ is NH;
$R^1$ is methyl;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ is NH;
$R^1$ is hydrogen;
$R^2$ is hydrogen;
$R^3$ is methoxy;
$R^5$ is 2-methoxymethyl, relative to the 1-position of the sulfonylamino group $SO_2$—NH;
$G^1$ is $CH_2$;
$G^2$ is $CH_2$; and
o is 0;
or
$X^1$ is NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2CH_2$; and
o is 1;
or
$X^1$ is NH;
$R^1$ is hydrogen;
$R^2$ is hydrogen;

$R^3$ is methoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2CH_2$;
$G^2$ is $CH_2$; and
o is 1;
or
$X^1$ is NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ is NH;
$R^1$ is methyl;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ is NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2$;
$G^2$ is $CH_2CH_2$; and
o is 1;
or
$X^1$ is NH;
$R^1$ is hydrogen;
$R^2$ is hydrogen;
$R^3$ is methoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;
$G^1$ is $CH_2CH_2$;
$G^1$ is $CH_2$; and
o is 1;
or
$X^1$ is NH;
$R^1$ is hydrogen;
$R^2$ is hydrogen;
$R^3$ is ethoxy;

$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ is NH;
R is methyl;
$R^2$ is hydrogen;
$R^3$ is ethoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2$; and
o is 1;
or
$X^1$ is NH;
$R^1$ is hydrogen;
$R^2$ is hydrogen;
$R^3$ is ethoxy;
$R^5$ is 2-methoxymethyl, relative to the 1-position of the sulfonylamino group $SO_2$—NH;
$G^1$ is $CH_2$;
$G^2$ is $CH_2$; and
o is 0;
or
$X^1$ is NH;
$R^1$ is hydrogen;
$R^2$ is hydrogen;
$R^3$ is ethoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2$;
$G^2$ is $CH_2CH_2$; and
o is 1;
or
$X^1$ is NH;
$R^1$ is hydrogen;
$R^2$ is hydrogen;
$R^3$ is ethoxy;
$R^5$ is 2-difluoromethoxy, relative to the 1-position of the sulfonylamino group $SO_2$—NH;
$R^6$ is 5-methyl, relative to the 1-position of the sulfonylamino group $SO_2$—NH and to the 2-position of 2-difluoromethoxy as radical $R^5$;
$G^1$ is $CH_2CH_2$;
$G^1$ is $CH_2$; and
o is 1;
or
$X^1$ is NH;
$R^1$ is hydrogen;
$R^2$ is hydrogen;
$R^3$ is ethoxy;
$R^5$ is 2-difluoromethoxy, relative to the 1-position of the sulfonylamino group $SO_2$—NH;
$R^6$ is 4-methyl, relative to the 1-position of the sulfonylamino group $SO_2$—NH and to the 2-position of 2-difluoromethoxy as radical $R^5$;

G¹ is CH₂;
G² is CH₂; and
o is 1;
or
X¹ is NH;
R¹ is methyl;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵;
G¹ is CH₂;
G² is CH₂; and
o is 1;
or
X¹ is NH;
R¹ is hydrogen;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵;
G¹ is CH₂;
G² is CH₂CH₂; and
o is 1;
or
X¹ is NH;
R¹ is hydrogen;
R² is hydrogen;
R³ is ethoxy;
R⁵ is 2-difluoromethoxy, relative to the 1-position of the sulfonylamino group SO₂—NH;
R⁶ is 4-methyl, relative to the 1-position of the sulfonylamino group SO₂—NH and to the 2-position of 2-difluoromethoxy as radical R⁵; G¹ is CH₂CH₂;
G¹ is CH₂; and
o is 1;
or
X¹ is NH;
R¹ is hydrogen;
R² is hydrogen;
R³ is methoxy;
R⁵ is 2-methoxymethyl, relative to the 1-position of the sulfonylamino group SO₂—NH;
G¹ is CH₂CH₂;
G² is CH₂; and
o is 0;
or
X¹ is NH;
R¹ is methyl;
R² is hydrogen;
R³ is methoxy;
R⁵ is 2-difluoromethoxy, relative to the 1-position of the sulfonylamino group SO₂—NH;
R⁶ is 5-methyl, relative to the 1-position of the sulfonylamino group SO₂—NH and to the 2-position of 2-difluoromethoxy as radical R⁵;
G¹ is CH₂CH₂;
G² is CH₂; and
o is 1.

19. The compound of claim 1, wherein at least one hydrogen atom has been replaced by a deuterium atom.

20. A pharmaceutical composition comprising at least one compound of claim 1, a stereoisomer, tautomer and/or physiologically tolerated acid addition salt thereof, and at least one physiologically acceptable carrier and/or auxiliary substance.

21. The compound of claim 1, or astereoisomer, tautomer, or physiologically tolerated acid addition salt thereof, selected from the group consisting of:
  N-(2-Difluoromethoxy-5-methyl-phenyl)-4-methoxy-3-pyrrolidin-3-yl-benzenesulfonamide;
  N-(2-Difluoromethoxy-5-methyl-phenyl)-4-methoxy-3-(1-methyl-pyrrolidin-3-yl)-benzenesulfonamide;
  4-Methoxy-N-(2-methoxymethyl-phenyl)-3-pyrrolidin-3-yl-benzenesulfonamide;
  N-(2-Difluoromethoxy-5-methyl-phenyl)-4-methoxy-3-pipendin-4-yl-benzenesulfonamide;
  N-(2-Difluoromethoxy-4-methyl-phenyl)-4-methoxy-3-pipendin-4-yl-benzenesulfonamide;
  4-Methoxy-N-(2-methoxymethyl-phenyl)-3-piperidin-4-yl-benzenesulfonamide; and
  N-(2-Difluoromethoxy-5-methyl-phenyl)-4-methoxy-3-(1-methyl-pipendin-4-yl)-benzenesulfonamide.

* * * * *